(12) United States Patent
Matsumoto et al.

(10) Patent No.: US 10,646,442 B2
(45) Date of Patent: *May 12, 2020

(54) LIPOSOME COMPOSITION AND METHOD FOR PRODUCING SAME

(71) Applicant: FUJIFILM Corporation, Tokyo (JP)

(72) Inventors: Takeshi Matsumoto, Kanagawa (JP); Kohei Ono, Kanagawa (JP); Makoto Ono, Kanagawa (JP); Kyoko Senga, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/335,640

(22) Filed: Oct. 27, 2016

(65) Prior Publication Data

US 2017/0042810 A1 Feb. 16, 2017

Related U.S. Application Data

(63) Continuation of application No. PCT/JP2015/062982, filed on Apr. 30, 2015.

(30) Foreign Application Priority Data

Apr. 30, 2014 (JP) .................................. 2014-094139

(51) Int. Cl.
*A61K 9/127* (2006.01)
*A61K 31/7068* (2006.01)
(Continued)

(52) U.S. Cl.
CPC ............ *A61K 9/127* (2013.01); *A61K 9/1278* (2013.01); *A61K 31/519* (2013.01);
(Continued)

(58) Field of Classification Search
CPC ...................................................... A61K 9/127
See application file for complete search history.

(56) References Cited

U.S. PATENT DOCUMENTS

| 5,094,854 A | 3/1992 | Ogawa et al. |
| 6,132,789 A * | 10/2000 | Sprott ............. A61K 9/1272 |
| | | 424/184.1 |

(Continued)

FOREIGN PATENT DOCUMENTS

| CN | 102716089 A * | 10/2012 |
| CN | 102784107 A * | 11/2012 |

(Continued)

OTHER PUBLICATIONS

S Arpicco, C Lerda, Ed Pozza, C Costanzo, N Tsapis, B Stella, M Donadelli, I Dando, E Fattal, L Cattel, M Palmieri. "Hyaluronic acid-coated liposomes for active targeting of genncitabine." European Journal of Pharmaceutics and Biopharmaceutics, vol. 85, 2013, pp. 373-380. (Year: 2013).*

(Continued)

*Primary Examiner* — Isaac Shomer
(74) *Attorney, Agent, or Firm* — Sughrue Mion, PLLC

(57) ABSTRACT

Provided are a liposome composition which has a practically required long-term preservation stability, and which has a release rate of a drug on the order of several tens of hours due to releasability of a drug being able to be suitably controlled by rendering an inner water phase hyper-osmotic; and a method for producing the same. According to the present invention, it is possible to provide a liposome composition, including liposomes each of which has an inner water phase and an aqueous solution which constitutes an outer water phase and in which the liposomes are dispersed, in which each of the liposomes encapsulates a drug in a dissolved state, an osmotic pressure of the inner water phase is 2-fold to 8-fold relative to the osmotic (Continued)

pressure of the outer water phase, and a release rate of the drug from each of the liposomes is 10%/24 hr to 70%/24 hr in blood plasma at 37° C.; and a method for producing the same.

9 Claims, 7 Drawing Sheets

(51) Int. Cl.
*A61K 47/24* (2006.01)
*A61K 47/28* (2006.01)
*A61K 31/519* (2006.01)
*A61K 45/00* (2006.01)

(52) U.S. Cl.
CPC .......... *A61K 31/7068* (2013.01); *A61K 45/00* (2013.01); *A61K 47/24* (2013.01); *A61K 47/28* (2013.01); *Y10S 977/773* (2013.01); *Y10S 977/906* (2013.01); *Y10S 977/907* (2013.01)

(56) References Cited

U.S. PATENT DOCUMENTS

| 10,391,057 | B2 * | 8/2019 | Ono | A61K 31/7068 |
|---|---|---|---|---|
| 2005/0249795 | A1 * | 11/2005 | Zhang | A61K 9/1272 424/450 |
| 2008/0213183 | A1 * | 9/2008 | Bally | A61K 9/127 424/9.2 |
| 2010/0292454 | A1 * | 11/2010 | Mishina | A61K 31/713 536/24.5 |
| 2011/0002977 | A1 * | 1/2011 | Li | A61K 9/1271 424/450 |

FOREIGN PATENT DOCUMENTS

| EP | 0 565 361 | A1 | 10/1993 | | |
|---|---|---|---|---|---|
| EP | 0565361 | A1 * | 10/1993 | ............. | A61K 9/127 |
| EP | 0565361 | A1 * | 10/1993 | ............. | A61K 9/127 |
| EP | 0 565 361 | B1 | 7/1996 | | |
| JP | H 02-001404 | A | 1/1990 | | |
| JP | H 06-009374 | A | 1/1994 | | |
| JP | 2007-536247 | A | 12/2007 | | |
| JP | 4971142 | B2 | 7/2012 | | |
| JP | 2013-508315 | A | 3/2013 | | |
| JP | 2013-126953 | A | 6/2013 | | |
| JP | 2013-526563 | A | 6/2013 | | |
| WO | 2005/021012 | A1 | 3/2005 | | |
| WO | 2005/107712 | A1 | 11/2005 | | |
| WO | 2007/005754 | A2 | 1/2007 | | |
| WO | 2011/047689 | A2 | 4/2011 | | |
| WO | 2011/047689 | A3 | 4/2011 | | |
| WO | 2011/144745 | A2 | 11/2011 | | |
| WO | 2011/144745 | A3 | 11/2011 | | |

OTHER PUBLICATIONS

C Bornmann, et al. "A new liposomal formulation of Gemcitabine is active in an orthotopic mouse model of pancreatic cancer accessible to bioluminescence imaging." Cancer Chemotherapy and Pharmacology, vol. 61, 2008, pp. 395-405. (Year: 2008).*
English Translation of CN 102716089 A. Obtained from https://patents.google.com/patent/CN102716089A/en?oq=gemcitabine+liposome on Jun. 12, 2018. 12 printed pages. Originally published Oct. 10, 2012. (Year: 2012).*
English Translation of CN 102784107 A. Obtained from https://patents.google.com/patent/CN102784107A/en?oq=gemcitabine+liposome on Jun. 12, 2018. 7 printed pages. Originally published Nov. 21, 2012. (Year: 2012).*
C Federico, VM Morittu, D Britti, E Trapasso, D Cosco. "Gemcitabine-loaded liposomes: rationale, potentialities and future perspectives." International Journal of Nanomedicine, vol. 7, 2012, pp. 5423-5436. (Year: 2012).*
H Gravem. "Gemcitabine-Containing Liposomes." Masters Thesis, University of Tromso, May 2006, pp. 1-86. (Year: 2006).*
JP May, MJ Ernsting, E Undzys, S-D Li. "Thermosensitive Liposomes for the Delivery of Gemcitabine and Oxaliplatin to Tumors." Molecular Pharmaceutics, vol. 10, 2013, pp. 4499-4508. (Year: 2013).*
D Paolino et al. "Gemcitabine-loaded PEGylated unilamellar liposomes vs GEMZAR®: Biodistribution, pharmacokinetic features and in vivo antitumor activity." Journal of Controlled Release, vol. 144, 2010, pp. 144-150. (Year: 2010).*
Q Zhou, L Liu, D Zhang, X Fan. "Preparation and characterization of gemcitabine liposome injections." Pharmazie, vol. 67, 2012, pp. 844-847. (Year: 2012).*
International Search Report for PCT/JP2015/062982 dated Jun. 9, 2015.
Written Opinion for PCT/JP2015/062982 dated Jun. 9, 2015.
International Preliminary Report on Patentability and translation of Written Opinion of the International Searching Authority dated Nov. 10, 2016, issued by the International Bureau in corresponding International Application No. PCT/JP2015/062982.
Extended European Search Report dated Jan. 2, 2017, from the European Patent Office in counterpart European Application No. 15786062.8.
Office Action dated Jun. 27, 2017, from the Japanese Patent Office in counterpart Japanese Application No. 2016-516405.

* cited by examiner

LIPOSOME COMPOSITION AND METHOD FOR PRODUCING SAME

CROSS-REFERENCE TO RELATED APPLICATIONS

The present application is a continuation of PCT/JP2015/062982 filed on Apr. 30, 2015 and claims priority under 35 U.S.C. § 119 of Japanese Patent Application No. 94139/2014 filed on Apr. 30, 2014.

BACKGROUND OF THE INVENTION

1. Field of the Invention

The present invention relates to a liposome composition and a method for producing the same. The present invention relates to a liposome composition which can be preferably used for pharmaceutical applications and a method for producing the same.

2. Description of the Related Art

A liposome (hereinafter, also referred to as lipid vesicle) is a closed vesicle formed of a lipid bilayer membrane using lipids, and has a water phase (inner water phase) within the space of the closed vesicle. Liposomes are usually present in a state of being dispersed in an aqueous solution (outer water phase) outside the closed vesicle. Liposomes have been studied for a variety of applications such as immune sensors, artificial red blood cells, and carriers of drug delivery systems taking advantage of features such as barrier capacity, compound retention capacity, biocompatibility, the degree of freedom of setting the particle size, ready biodegradability, and surface-modifying properties. In carrier applications, liposomes can encapsulate water-soluble compounds, lipophilic low-molecular weight materials, polymers and a wide range of materials.

In the case where liposomes are used particularly as a carrier for a drug delivery system, it is necessary to make a particle size to be about 200 nm or less in terms of permeation through a biological membrane. Further, in a carrier for a drug delivery system, it is also necessary to have liposomes which form particles having a good dispersibility under the temperature conditions of about 37° C. which is the body temperature of a mammal. In particular, with regard to nano-sized fine particles, it is preferred to impart preservation stability from various viewpoints such as aggregation, precipitation, and leakage of drugs.

As a carrier for a drug delivery system, in the case where a drug (solution or the like containing liposomes containing a drug) is administered by intravenous injection, high safety is required for an intravenous injection product. Additives such as chlorinated solvents, for example chloroform, or dispersing aids whose use are not allowed are undesirable. In addition, impartment of stability to a pharmaceutical product is also necessary, and correspondingly suppression of drug leakage, lipid decomposition or the like after storage is required. Further, suitability for sterile filtration is also required in order to guarantee sterility. When it is desired to produce liposomes as a pharmaceutical product on an industrial scale, it is necessary to take into account the requirements as described above.

WO2005/021012A discloses a gemcitabine-encapsulating pharmaceutical carrier which is capable of suppressing a release rate of gemcitabine and is capable of maintaining a local concentration of gemcitabine for a long period of time. Further, this patent document discloses that a suitable release rate is exhibited by cholesterols being contained as membrane components in a specific proportion. Further, this patent document discloses a drug carrier containing gemcitabine-encapsulated liposomes in a carrier containing cholesterols in a proportion of 0 mol % or more and less than 35 mol %, together with phospholipids. Further, this patent document also discloses that the release rate of a drug from liposomes declines as the proportion of cholesterol decreases.

JP4971142B discloses an aqueous solution containing liposomes in an aqueous medium, where each liposome has an aqueous internal space isolated from the medium by a membrane containing cholesterol and phosphatidylcholine, and the internal space contains supplementary irinotecan and sucrose octasulfate. Further, although this liposome composition allows a sufficiently high intraliposomal osmotic pressure of 727 mmol/kg, there may be a case where drugs that can be used in the liposomes are limited because the Examples use polyanions such as sucrose octasulfate. Further, Example 64 describes the preparation of an aqueous solution having an osmotic pressure of 727 mmol/kg. However, there is no mention of preservation stability or releasability of this aqueous solution.

In all of the above-mentioned documents, a liposome composition having a practically required long-term preservation stability and also having a suitable release rate and a method for producing the same have not been fully established, and correspondingly improvements are desired.

SUMMARY OF THE INVENTION

In a method of adsorbing and retaining a drug onto a lipid membrane of a liposome, release of the drug to the outside of the liposome becomes difficult due to strong interactions such as hydrophobic interactions and electrostatic interactions. Therefore, the configuration of the liposome composition after production can be maintained, whereby it is easy to secure long-term preservation stability.

In this case, it becomes difficult to release a drug to an affected area since interactions are too strong. Therefore, it is ideal to encapsulate a drug in a dissolved state in an inner water phase of a liposome, and also a liposome composition is rendered to have hyper-osmotic conditions, thus promoting release of the drug from the liposome composition, whereby it is possible to realize more suitable drug delivery. However, rendering to have hyper-osmotic conditions results in ready leakage of the drug from the liposome composition, so it is difficult to ensure long-term preservation stability.

Further, in the case where it is desired to effectively deliver a drug to an affected area, it is preferable that liposomes are fine particles having an average particle size of 100 nm or less. However, microparticulation contributes to an increase in the curvedness (curvature) of a liposome membrane, thus resulting in difficulty of encapsulating a drug.

In the case where the drug contained in a liposome is an anticancer agent, there are anticancer agents whose attack on cancer cells is greatly affected by an exposure time to the drug. For example, since a drug such as a metabolic antagonist that inhibits DNA synthesis attacks only some of cells in the DNA synthesis phase, effective cytocidal effects cannot be obtained if an exposure time is short. In such a drug, the expected drug efficacy is not obtained in many cases since a sufficient exposure time in tumors cannot be achieved if metabolism in the body after administration is fast.

In addition, although there are also methods of administration achieving prolonged exposure by an intravenous drip of a dilute concentration of an anticancer agent in order to obtain a sufficient exposure time, these are unfavorable from the viewpoint of quality of life (QOL), such as a patient being restrained during the intravenous drip time.

The present invention has been made in view of the foregoing circumstances, and an object of the present invention is to provide a liposome composition which has a practically required long-term preservation stability, and which has a release rate of a drug on the order of several tens of hours due to releasability of a drug being able to be suitably controlled by rendering an inner water phase hyper-osmotic; and a method for producing the same.

As a result of extensive studies, the present inventors have discovered a liposome composition which has a long-term preservation stability required for practical use, and which has a release rate of a drug on the order of several tens of hours due to releasability of a drug being able to be suitably controlled by rendering an inner water phase hyper-osmotic, and a method for producing the same. The present invention has been completed based on this discovery. That is, according to the present invention, there is provided a liposome composition, comprising:

liposomes each of which has an inner water phase and an aqueous solution which constitutes an outer water phase and in which the liposomes are dispersed, wherein each of the liposomes encapsulates a drug in a dissolved state, an osmotic pressure of the inner water phase is 2-fold to 8-fold relative to the osmotic pressure of the outer water phase, and a release rate of the drug from each of the liposomes is 10%/24 hr to 70%/24 hr in blood plasma at 37° C.

In the liposome composition of the present invention, the following aspects are preferred.

Preferably, the drug is at least one of an anticancer agent or a metabolic antagonist.

Preferably, lipids constituting the liposome include at least hydrogenated soybean phosphatidylcholine, 1,2-distearoyl-3-phosphatidylethanolamine-polyethylene glycol, and cholesterol.

Preferably, an average particle size of the liposomes is 5 nm to 100 nm.

Preferably, the release rate of the drug from the liposome is 10%/24 hr or less in physiological saline containing no blood components at 37° C.

The present invention is a pharmaceutical composition comprising the above-described liposome composition.

The present invention is a method for producing a liposome composition, comprising:

an emulsifying step of emulsifying lipids dissolved in an organic solvent to form liposomes, without a drying and solidifying step;

a drug loading step of encapsulating a water-soluble drug in the liposomes obtained in the emulsifying step; and an osmotic pressure adjusting step of replacing an unencapsulated drug aqueous solution with a hypo-osmotic solution to adjust the osmotic pressure of an inner water phase to be hyper-osmotic relative to the osmotic pressure of an outer water phase.

In the method for producing a liposome composition according to the present invention, the following aspects are preferred.

Preferably, the osmotic pressure adjusting step adjusts the osmotic pressure of the inner water phase of the liposomes to 2-fold to 8-fold relative to the osmotic pressure of the outer water phase.

Preferably, the liposomes obtained after the emulsifying step are used in a next step without extrusion processing.

Preferably, the drug loading step and the osmotic pressure adjusting step are carried out simultaneously.

According to the liposome composition of the present invention, it is possible to provide a liposome composition which has a practically required long-term preservation stability, and which has a release rate of a drug on the order of several tens of hours due to releasability of a drug being able to be suitably controlled by rendering an inner water phase hyper-osmotic; and a method for producing the same.

DESCRIPTION OF THE PREFERRED EMBODIMENTS

Figure 1:
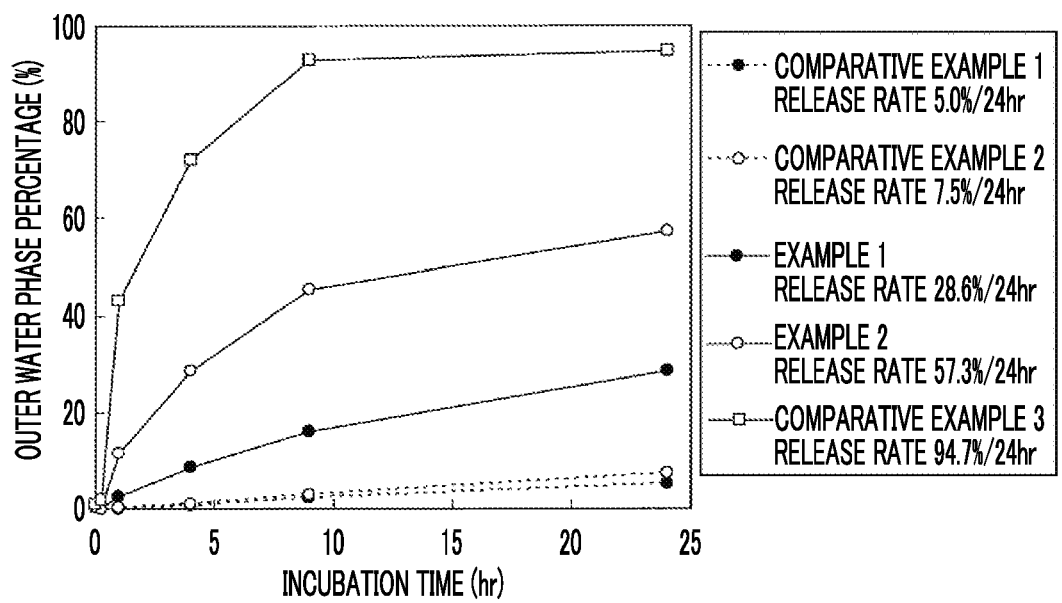
FIG. 1 is a plot of a relationship between an incubation time and an outer water phase percentage.

The term "step" as used herein includes not only an independent step, but also a step which may not be clearly separated from another step, insofar as an expected effect of the step can be attained.

The numerical value ranges shown with "to" in the present specification means ranges including the numerical values indicated before and after "to" as the minimum and maximum values, respectively.

In the present invention, unless otherwise specified, % means mass percent.

In referring herein to a content of a component in a composition, in a case where plural substances exist corresponding to a component in the composition, the content means, unless otherwise specified, the total amount of the plural substances existing in the composition.

The "encapsulation rate" refers to a ratio (mass ratio or molar ratio) of a drug encapsulated in a liposome to an incorporated drug (charged amount), when liposome constituents and a drug are incorporated to form an encapsulated drug carrier.

The "release" means that the drug encapsulated in a liposome passes through the lipid membrane constituting the liposome and then exits to the outside of the liposome.

The "release rate" refers to a ratio (weight ratio or molar ratio) of a drug exiting to the outside from a liposome in which liposome constituents and a drug are encapsulated to a drug encapsulated in the liposome.

The "release rate is slow" means that an amount of the drug exiting to the outside of a liposome per unit time is small.

The "retentivity in blood" means a property (state) of which a drug in a state of being encapsulated in a liposome is present in blood, in a target ("subject" or "individual", preferably a mammal such as a human (patient), a mouse, a monkey, or a domestic animal) to which a liposome composition (or a pharmaceutical composition containing the liposome composition) has been administered.

The "tumor" (which is used interchangeably with "cancer" in the present invention) specifically includes solid tumors such as esophageal cancer, stomach cancer, colon cancer, rectal cancer, liver cancer, laryngeal cancer, lung cancer, prostate cancer, bladder cancer, breast cancer, uterine cancer, ovarian cancer, and Kaposi's sarcoma, and liquid tumors such as leukemia. Sites where a tumor occurs are cells, tissues, organs or intestines and the inside thereof.

Hereinafter, the present invention will be described in detail.

The present invention is a liposome composition including liposomes each of which has an inner water phase and an aqueous solution which constitutes an outer water phase and in which the liposomes are dispersed, in which each of the liposomes encapsulates a drug in a dissolved state, the osmotic pressure of the inner water phase is 2-fold to 8-fold relative to the osmotic pressure of the outer water phase, and the release rate of the drug from each of the liposomes is 10%/24 hr to 70%/24 hr in blood plasma at 37° C.

(Liposome)

The liposome is a closed vesicle formed of a lipid bilayer membrane using lipids, and has a water phase (inner water phase) within the space of the closed vesicle. The inner water phase contains water and the like. The liposome is usually present in a state of being dispersed in an aqueous solution (outer water phase) outside the closed vesicle. The liposome may be single lamellar (which is also referred to as monolayer lamellar or unilamellar, and is a structure having a single bilayer membrane) or multilayered lamellar (which is also referred to as multilamellar and is an onion-like structure having multiple bilayer membranes where individual layers are compartmented by aqueous layers). In the present invention, a single lamellar liposome is preferred from the viewpoint of safety and stability in pharmaceutical applications.

The liposome is not particularly limited in terms of form as long as it is a liposome capable of encapsulating a drug. The "encapsulating" means taking a form where a drug is contained in an inner water phase with respect to the liposome. For example, the liposome may be a form where a drug is encapsulated within a closed space formed of a membrane, a form where a drug is included in the membrane itself, or a combination thereof.

The size (average particle size) of a liposome is not particularly limited, and it is 2 to 200 nm, preferably 5 to 150 nm, more preferably 5 to 120 nm, and still more preferably 5 to 100 nm. In the present invention, the "average particle size" means an average value of diameters of liposomes as measured by a light scattering method.

The liposome is preferably in the form of a spherical shape or a morphology close thereto.

The component (membrane component) constituting the lipid bilayer of a liposome is selected from lipids. As the lipid, any one may be used as long as it is dissolved in a mixed solvent of a water-soluble organic solvent and an ester-based organic solvent. Specific examples of lipids include phospholipids, lipids other than phospholipids, cholesterols and derivatives thereof. These components may be composed of single or plural components.

Examples of the phospholipid include natural or synthetic phospholipids such as phosphatidylcholine (lecithin), phosphatidyl glycerol, phosphatidic acid, phosphatidyl ethanolamine, phosphatidyl serine, phosphatidyl inositol, sphingomyelin, and cardiolipin, or hydrogenated products thereof (for example, hydrogenated soybean phosphatidylcholine (HSPC)). Among these, preferred is a hydrogenated phospholipid such as hydrogenated soybean phosphatidylcholine, or sphingomyelin, and more preferred is hydrogenated soybean phosphatidylcholine. In the present invention, the "phospholipid" also encompasses a phospholipid derivative in which the phospholipid is modified.

Lipids other than phospholipids may be lipids containing no phosphoric acid, and examples thereof include, but are not particularly limited to, glycerolipid which does not contain a phosphoric acid moiety in the molecule, and sphingolipid which does not contain a phosphoric acid moiety in the molecule. In the present invention, the term "lipids other than phospholipids" also encompasses derivatives of lipids other than phospholipids in which modifications have been made to lipids other than phospholipids.

In the case where the lipid other than phospholipid contains a basic functional group, for example, in the case where the lipid other than phospholipid is a material where a compound having a basic functional group is bonded to a lipid, the lipid is referred to as a cationized lipid. The cationized lipid, for example, becomes possible to modify the membrane of the liposome and therefore can enhance the adhesion to cells which are target sites.

Examples of the cholesterols include cholesterol. When the average particle size decreases to 100 nm or less, the curvature of the lipid membrane becomes higher. Since the deformation of the membrane arranged in the liposome also becomes larger, a water-soluble drug becomes more susceptible to leakage. However, as a means for suppressing leakage properties, it is effective to add cholesterol or the like in order to fill the deformation of the membrane caused by lipid.

In addition to the above-mentioned components, a hydrophilic polymer or the like for improving retentivity in blood, fatty acid, diacetyl phosphate or the like as a membrane structure stabilizer, or α-tocopherol or the like as an antioxidant may be added to the liposome. In the present invention, it is preferable not to use additives such as a dispersing aid not authorized for intravenous injection use in pharmaceutical applications, for example, a surfactant or the like.

The liposome of the present invention preferably contains hydrophilic polymer-modified products of phospholipids, lipids other than phospholipids, or cholesterols as phospholipids, lipids other than phospholipids, cholesterols and derivatives thereof.

Examples of the hydrophilic polymer include, but are not particularly limited to, polyethylene glycols, polyglycerols, polypropylene glycols, polyvinyl alcohols, a styrene-maleic anhydride alternating copolymer, polyvinylpyrrolidone, and synthetic polyamino acid. The above-mentioned hydrophilic polymers may be used alone or in combination of two or more thereof.

Among these, from the viewpoint of retentivity in blood of a formulation, preferred are polyethylene glycols, polyglycerols, or polypropylene glycols, and more preferred is polyethylene glycol (PEG), polyglycerol (PG), or polypropylene glycol (PPG). Polyethylene glycol (PEG) is most commonly used and is preferable due to having an effect of improving retentivity in blood.

The molecular weight of PEG is not particularly limited. The molecular weight of PEG is 500 to 10,000 daltons, preferably 1,000 to 7,000 daltons, and more preferably 2,000 to 5,000 daltons.

In the liposome of the present invention, it is preferable to use a lipid modified by PEG (PEG-modified lipid), together with the main lipid contained in the liposome. Examples of the PEG-modified lipid include 1,2-distearoyl-3-phosphatidylethanolamine-polyethylene glycol such as 1,2-distearoyl-3-phosphatidylethanolamine-PEG2000 (manufactured by Nippon Oil & Fats Co., Ltd.), 1,2-distearoyl-3-phosphatidylethanolamine-PEG5000 (manufactured by Nippon Oil & Fats Co., Ltd.) and distearoyl glycerol-PEG2000 (manufactured by Nippon Oil & Fats Co., Ltd.). These PEG-modified lipids may be added in an amount of 0.3 to 50 mass %, preferably 0.5 to 30 mass %, and more preferably 1 to 20 mass % with respect to total lipid content.

In the liposome of the present invention, preferred is a lipid combination of hydrogenated soybean phosphatidylcholine (a main lipid contained in liposome), 1,2-distearoyl-3-phosphatidylethanolamine-polyethylene glycol (a lipid used in combination with the main lipid), and cholesterol.

The liposome composition of the present invention preferably does not contain an anionic polymer (polyanion). In the present invention, since it is possible to control the releasability by means of an osmotic pressure of an inner water phase, there are advantages in that general versatility is excellent, and drugs which can be used in liposomes are not limited.

(Drug)

The liposome of the present invention may contain at least one of water-soluble drugs as a drug.

In the case of a water-soluble drug, a form to be retained in the inner water phase of the liposome is advantageous, but there may be a case where a drug becomes readily susceptible to leakage because the lipid bilayer membrane is thin and soft. However, according to the method for producing a liposome of the present invention, it is possible to produce a liposome having safety and stability even when the particle size of the liposome is set to about 100 nm or less.

The drug encompassed by the drug may be any water-soluble drug that can be encapsulated in liposomes, and specific examples thereof include, but are not limited to, water-soluble materials having a physiological activity or a pharmacological activity such as enzymes, proteins, peptides, nucleic acids (DNA, mRNA, siRNA, miRNA), low molecular weight compounds, sugars (oligosaccharides and polysaccharides), polymer compounds, antitumor agents, antimicrobial agents, contrast agents, antioxidants, anti-inflammatory agents, whitening agents, humectants, and hair growing agent. In the case of using a liposome as a carrier for a drug delivery system, the water-soluble drug is preferably a low-molecular weight compound from the viewpoint of stability.

Specific examples of the water-soluble drug include anticancer agents such as an anthracycline-based anticancer agent such as doxorubicin, daunorubicin or epirubicin, a cisplatin-based anticancer agent such as cisplatin or oxaliplatin, a taxane-based anticancer agent such as paclitaxel or docetaxel, a vinca alkaloid-based anticancer agent such as vincristine or vinblastine, a bleomycin-based anticancer agent such as bleomycin, and a sirolimus-based anticancer agent such as sirolimus, and metabolic antagonists such as methotrexate, fluorouracil, gemcitabine, cytarabine, and pemetrexed. Among these, preferred is a water-soluble drug such as doxorubicin, gemcitabine, or pemetrexed.

(Water-Soluble Drug Encapsulated in Dissolved State)

The water-soluble drug encapsulated in the liposome of the present invention is present in a dissolved state in the inner water phase of the liposome. Here, with regard to the dissolved state, it is deemed to have been encapsulated in a dissolved state in a case where the amount of the drug filled with respect to the volume of the liposome is below the saturation solubility of the drug in the composition liquid of the inner water phase. Further, even when the amount of the drug filled is above the saturation solubility of the drug, a case where drug crystals are not observed by Cryo-TEM and diffraction patterns attributable to crystal lattice are not observed by XRD measurement indicates that most of the drug is dissolved due to acceleration of dissolution by physicochemical environment created by the lipid membrane, partial incorporation of the drug into the lipid membrane or the like and is deemed to have been encapsulated in a dissolved state. Further, a case which is encapsulated by a loading method of encapsulating a drug via the formation of a solid inside the liposome is not the dissolved state referred to in the present invention, even when the drug is a highly water-soluble drug.

The water-soluble drug to be encapsulated in a dissolved state preferably has a solubility in water of 1 mg/ml or more, and more preferably a solubility in water of 10 mg/ml or more.

(Method for Producing Liposome Composition)

The method for producing a liposome according to the present invention is a method for producing a liposome composition including:

an emulsifying step of emulsifying lipids dissolved in an organic solvent to form a liposome, without a drying and solidifying step;

a drug loading step of encapsulating a water-soluble drug in the liposome obtained in the emulsifying step; and a drug loading step of adjusting an osmotic pressure of an inner water phase of the liposome to 2-fold to 8-fold relative to the osmotic pressure of an outer water phase.

The method for producing a liposome composition may include, if desired, other steps such as an evaporating step of evaporating the organic solvent used in the emulsifying step.

The emulsifying step of emulsifying lipids dissolved in an organic solvent to form a liposome, without a drying and solidifying step, is not limited as long as it is a step of emulsification, but it is preferably a step of applying a high shearing force and performing microparticulation with an emulsifying step including an organic solvent. If necessary, evaporation (desolvation) of the organic solvent used in the emulsifying step may be carried out to form a liposome.

(Emulsifying Step)

In the emulsifying step, an oil phase where at least one lipid has been dissolved in an organic solvent and a water phase are mixed to prepare an aqueous solution containing lipids, which is then emulsified with stirring. An oil phase where lipids have been dissolved in an organic solvent and a water phase are mixed, stirred and emulsified to thereby prepare an emulsion where an oil phase and a water phase are emulsified in an O/W type. After mixing, a liposome is formed by removing a portion or all of the organic solvent derived from the oil phase using an evaporating step to be described below. Alternatively, a portion or all of the organic solvent in the oil phase is evaporated in the course of the stirring-emulsification to form a liposome.

As a method of stirring, ultrasonic waves or mechanical shearing force is used for particle miniaturization. In addition, extruder processing of allowing to pass through a filter having a certain pore diameter or microfluidizer processing may be carried out for uniformity of particle sizes. Use of an extruder or the like can result in decomposition of secondarily formed multivesicular liposomes into univesicular liposomes. In the present invention, it is preferred from the viewpoint of simplification of the production process that a liposome in a state of a drug being not loaded is used in the next step without extrusion processing.

In the present invention, an average particle size of a liposome to be prepared can be controlled by arbitrarily selecting the speed and time of stirring. In view of obtaining a liposome having safety and stability, it is preferable to provide shearing at a circumferential speed of 20 m/sec or higher to an aqueous solution containing lipid. The shearing is not limited, and a specific example thereof is preferably shearing at a circumferential speed of 20 m/sec to 35 m/sec, and more preferably shearing at a circumferential speed of 23 m/sec to 30 m/sec.

(Oil Phase)

As the organic solvent serving as an oil phase, a mixed solvent of a water-soluble organic solvent and an ester-based organic solvent is used. In the present invention, it is preferred that an organic solvent such as chloroform, methylene chloride, hexane, or cyclohexane is not substantially used as the organic solvent, and it is more preferred that these organic solvents are not used at all.

The water-soluble organic solvent is not particularly limited, and it is preferably an organic solvent having a property that is optionally miscible with water. Specific examples of the water-soluble organic solvent include alcohols such as methanol, ethanol, n-propanol, isopropanol, n-butanol, isobutanol, and t-butanol; glycols such as glycerol, ethylene glycol, and propylene glycol; and polyalkylene glycols such as polyethylene glycol. Among these, preferred are alcohols. The alcohol is preferably at least one selected from ethanol, methanol, 2-propanol, or t-butanol, more preferably at least one selected from ethanol, 2-propanol, or t-butanol, and still more preferably ethanol.

The ester-based organic solvent is not particularly limited, and it is preferably an ester obtained from the reaction of organic acids and alcohols. Specifically, the ester-based organic solvent is preferably at least one selected from ethyl acetate, methyl acetate, isopropyl acetate, t-butyl acetate, or methyl propionate, more preferably ethyl acetate, isopropyl acetate, or methyl propionate, and still more preferably ethyl acetate.

The mixing ratio of water-soluble organic solvent:ester-based organic solvent is not particularly limited, and it may be 90:10 to 30:70, preferably 80:20 to 40:60, and more preferably 80:20 to 70:30 by mass ratio. The mixed solvent of a water-soluble organic solvent and an ester-based organic solvent may further contain an aqueous solvent to be described below, such as water or buffer. The aqueous solvent may be added in a range of, for example, 1 to 30 mass %. The pH of the mixed solvent is not particularly limited, and it is preferably in the range of about 3 to 10, and more preferably about 4 to 9. The ester-based organic solvents may contain physiologically active substances or the like such as various medicines which are soluble in these solvents.

In the case where ethanol is used as the water-soluble organic solvent and ethyl acetate is used as the ester-based organic solvent, the mixing ratio of ethanol:ethyl acetate is not particularly limited, and it is preferably 80:20 to 70:30 by a mass ratio.

The concentration of the lipid is not particularly limited and may be appropriately adjusted, but it may be 40 g/L to 250 g/L, preferably 100 g/L to 200 g/L in terms of a solution where a mixed solution of a water-soluble organic solvent and an ester-based organic solvent serves as a solvent.

(Water Phase)

The water phase means an outer water phase and an inner water phase.

The outer water phase as used herein means an aqueous solution in which the liposomes are dispersed. For example, in the case of an injection, a solution occupying the outside of the liposome of a dispersion liquid of liposomes packaged and stored in a vial or prefilled syringe becomes an outer water phase. Also, similarly for a liquid to be dispersed at the time of use when administered by means of an attached dispersion solution or other solutions, a solution occupying the outside of the liposome of a dispersion liquid of liposomes becomes an outer water phase.

The inner water phase as used herein means a water phase in the closed vesicle with a lipid bilayer membrane therebetween.

As a liposome-dispersing aqueous solution (outer water phase) when producing liposomes, water (distilled water, water for injection, or the like), physiological saline, various buffers, an aqueous solution of sugars or a mixture thereof (aqueous solvent) is preferably used. The buffer is not limited to organic and inorganic buffer solutions, and a buffer having a buffering action in the vicinity of a pH close to that of the body fluid is preferably used and examples thereof include phosphate buffer, tris buffer, citrate buffer, acetate buffer, and Good's buffer. The pH of the water phase is not particularly limited, and it may be 5 to 9, preferably 7 to 8. For example, a phosphate buffer (for example, pH=7.4) is preferably used. The inner water phase of the liposome may be a liposome-dispersing aqueous solution when producing liposomes, or may be water, physiological saline, various buffers, an aqueous solution of sugars or a mixture thereof which are newly added. The water used as an outer water phase or an inner water phase is preferably free from impurities (dust, chemicals, or the like).

The physiological saline refers to an inorganic salt solution adjusted to be isotonic with the human body fluid, and may further have a buffering function. Examples of the physiological saline include saline containing 0.9 w/v % of sodium chloride, phosphate buffered saline (hereinafter, also referred to as PBS), and tris buffered saline.

(Evaporating Step)

In the present invention, an evaporating step may be provided if necessary. In the evaporating step, an organic solvent is evaporated from the aqueous solution containing the liposomes obtained in the emulsifying step. In the present invention, the evaporating step includes at least one of a step of forcibly removing a portion or all of the organic solvent derived from the oil phase as an evaporating step, and a step of naturally evaporating a portion or all of the organic solvent in the oil phase during the course of stirring-emulsification.

The method of evaporating an organic solvent in the evaporating step is not particularly limited. For example, at least one of a step of heating to evaporate an organic solvent, a step of continuing the standing or slow stirring after emulsification, or a step of performing vacuum degassing may be carried out.

In the present invention, in the step of evaporating an organic solvent, it is preferred that the concentration of an organic solvent contained in an aqueous solution containing liposomes is to be 15% by mass or less within 30 minutes from after the start of a step of evaporating the organic solvent.

A liquid temperature when carrying out the production method of the present invention can be appropriately adjusted, but the liquid temperature at the time of mixing an oil phase and a water phase is preferably higher than or equal to a phase transition temperature of the lipid to be used. For example, in the case where a lipid having a phase transition temperature of 35° C. to 40° C. is used, the liquid temperature is preferably set to 35° C. to 70° C.

The aqueous solution containing the liposomes prepared via an emulsifying step may be subjected to post-processing such as centrifugation, ultrafiltration, dialysis, gel filtration, or freeze-drying, for removal of components that had not been included in the liposomes, or adjustment of a concentration and an osmotic pressure.

Particle sizes of the resulting liposomes can be made uniform by using dialysis, filtration, extrusion processing, or the like. In the method for producing a liposome composition according to the present invention, it is preferred to prepare empty liposomes in a state where a drug is not loaded, without subjecting to extrusion processing. Moreover, if it is desired to separate the drug encapsulated in liposomes from the drug not encapsulated in liposomes, centrifugation, dialysis, gel filtration, or the like may be employed.

(Extrusion Processing)

Extrusion processing means a step of passing liposomes through a filter having a fine pore to apply a physical shear force, thereby performing microparticulation. When the liposomes are passed through, rapid microparticulation may be achieved by incubating the liposome dispersion liquid and the filter at a temperature higher than or equal to the phase transition temperature of the membrane constituting the liposome.

(Drug Loading Step)

In the drug loading step of the present invention, in the case of encapsulating a water-soluble drug in liposomes, the drug can be encapsulated in the inner water phase of the liposome by a method of dissolving the drug in an aqueous medium capable of performing hydration and swelling, followed by heating at a temperature higher than or equal to the phase transition temperature, and sonication or extrusion. A drug may also be encapsulated in an inner water phase by dissolving the drug in the water phase at a time of lipid emulsification.

(Osmotic Pressure Adjusting Step)

In the present invention, it becomes easy to release a drug by rendering the inner water phase of the liposomes hyper-osmotic (pressure difference) through an osmotic pressure adjusting step. The release rate can be controlled by setting the osmotic pressure. The osmotic pressure adjusting step is not particularly limited, and a method such as dialysis after the drug loading step may be employed. This makes it possible to adjust the osmotic pressure. In the present invention, it is preferable to carry out the drug loading step and the osmotic pressure adjusting step (preferably adjusting of the osmotic pressure of an inner water phase) at the same time, from the viewpoint of production efficiency.

In the present invention, by controlling the release, for example, in the case of using the liposome of the present invention as a drug delivery system, it is possible to release the required amount of the drug that is needed in an affected area to be targeted. However, a hyper-osmotic liposome is easy to release a drug, but becomes easy to leak a drug during storage, so it is difficult to achieve both good releseability and preservation stability. According to the liposome composition of the present invention, it has an unexpected effect capable of achieving both easy release and preservation stability of a drug by setting the osmotic pressure of the inner water phase to 2-fold to 8-fold relative to the osmotic pressure of outer water phase, for liposomes having an inner water phase obtained from the emulsified lipids.

In general, as a method for rendering an inner water phase hyper-osmotic, for example, there is a method of making an inner water phase and an outer water phase of a liposome in which a drug has not encapsulated to have a high osmotic pressure, and then lowering the osmotic pressure of the outer water phase by dialysis or the like. In that case, in a subsequent drug loading step to be performed, there may be a case where the drug contained in the inner water phase is leaked, and also the osmotic pressure of the inner water phase is decreased.

Therefore, in the present invention, along with loading of a drug, an inner water phase is replaced with a solution of a high osmotic pressure, and then removal of the drug in an outer water phase and lowering of the outer water phase osmotic pressure are carried out simultaneously by dialysis, whereby it is possible to obtain a liposome composition capable of achieving both easy release and preservation stability of a drug.

In the liposome of the present invention, the osmotic pressure of the inner water phase is 2-fold to 8-fold, preferably 2.5-fold to 6-fold, more preferably 3-fold to 5-fold, with respect to the osmotic pressure of the outer water phase. By setting to be 2-fold or higher-fold, the lipid bilayer membrane of the liposome is generally known to show a structure such as a double membrane structure or an interdigitated structure. When the osmotic pressure of the inner water phase is 2-fold or higher-fold with respect to the outer water phase, the liposome begins to change from a double membrane structure into an interdigitated structure. In the present invention, in order to take a suitable interdigitated structure, it is preferable to control the osmotic pressure of the inner water phase by adjusting a cholesterol proportion, although the conditions for various lipids may be set up. As a result, it is possible to obtain a liposome composition capable of achieving both the easy release and preservation stability of a drug.

In the liquid obtained after the final drug loading step, solutes of outer water phase and the inner water phase are homogenized, and the osmotic pressure at that time can be defined as an osmotic pressure of an inner water phase of the liposome composition to be completed. However, in a subsequent replacement-osmotic pressure adjusting step by dialysis of the outer water phase, a heating operation is limited only to a case where the solutes of the inner water phase are sufficiently retained, such as being suppressed below phase transition of a lipid. In addition, the osmotic pressure of the outer water phase can be defined as an osmotic pressure of a dialysis liquid used in the final dialysis step. However, this is limited only to a case where the outer water phase was sufficiently replaced with a dialysis liquid. Further, for the finished solution of a liposome composition, it is also possible to obtain the osmotic pressure of the inner water phase and the outer water phase by quantifying the composition concentration of the solute in the outer water phase and the composition concentration of the solute in the inner water phase using centrifugation or ultrafiltration, and measuring the osmotic pressure of the composition liquid.

Measurement of an osmotic pressure may be carried out according to an osmolality measurement method described in the sixteenth revised Japanese Pharmacopoeia. Specifically, it is possible to determine osmolality by measuring the degree of freezing point (ice point) depression of water. In addition, the degree of freezing point depression of water is defined in terms of solute molar concentration, and it is also possible to determine osmolality from the solute molar concentration.

The osmotic pressure of the outer water phase in the present invention has a significant effect on the living body upon administration. In the case where the osmotic pressure of the outer water phase is far away from the osmotic pressure of a body fluid, hemolysis or pain caused by the movement of moisture in individual tissues occurs. Therefore, the osmotic pressure of the outer water phase in the present invention is preferably 200 to 400 mOsmol/L, more preferably 250 to 350 mOsmol/L, and most preferably isotonic with the body fluid.

(Sterile Filtration)

In order to formulate an aqueous solution containing liposomes, obtained by the method for producing a liposome composition according to the present invention, into a pharmaceutical composition, it is preferable to carry out sterile filtration. Regarding the filtration method, it is possible to remove unwanted materials from the aqueous solution containing liposomes by using a hollow fiber membrane, a reverse osmosis membrane, a membrane filter or the like. In the present invention, the aqueous solution containing liposomes is preferably filtered using a filter having a sterile pore size (preferably 0.2 μm sterile filter) although there is no particular limitation. Normally, adsorption or aggregation of liposomes onto a sterile filter may occur in the filtration step. However, the present invention has unexpected effects such as little influence of pressure loss or the like when performing filtration, since liposomes having a specific average particle size and uniform particle size distribution are obtained.

To prevent an effect of liposome deformation on the average particle size, the sterile filtration step and the below-described aseptic filling step are preferably carried out at a temperature lower than or equal to the phase transition temperature of the lipid constituting the liposome. For example, in the case where the phase transition temperature of the lipid is around 50° C., the sterile filtration step and the below-described aseptic filling step are carried out at temperature of preferably about 0° C. to 40° C., and more specifically about 5° C. to 30° C.

(Aseptic Filling)

The aqueous solution containing the liposomes obtained after sterile filtration is preferably aseptically filled for medical applications. Known methods can be applied for aseptic filling. A liposome composition suitable for medical applications can be prepared by aseptically filling the liposome-containing aqueous solution in a container.

An aqueous solvent, an additive, or the like may be appropriately added to the aqueous solution containing the liposomes obtained by the present invention to thereby prepare a pharmaceutical composition containing a liposome composition. In connection with the route of administration, the pharmaceutical composition may also contain at least one of a tonicity agent, a stabilizer, an antioxidant, or a pH adjusting agent which is pharmaceutically acceptable.

The tonicity agent is not particularly limited and examples thereof include inorganic salts such as sodium chloride, potassium chloride, sodium hydrogen phosphate, sodium dihydrogen phosphate, and potassium dihydrogen phosphate; polyols such as glycerol, mannitol, and sorbitol; and sugars such as glucose, fructose, lactose, and sucrose.

The stabilizer is not particularly limited and examples thereof include sugars such as glycerol, mannitol, sorbitol, lactose, and sucrose.

The antioxidant is not particularly limited and examples thereof include ascorbic acid, uric acid, tocopherol homologues (for example, vitamin E, four tocopherol isomers α, β, γ, and δ), cysteine, and EDTA. Stabilizers and antioxidants may be respectively used alone or in combination of two or more thereof.

Examples of the pH adjusting agent include sodium hydroxide, citric acid, acetic acid, triethanolamine, sodium hydrogen phosphate, sodium dihydrogen phosphate, and potassium dihydrogen phosphate.

The pharmaceutical composition of the present invention may contain an organic solvent, collagen, polyvinyl alcohol, polyvinyl pyrrolidone, a carboxyvinyl polymer, sodium carboxymethyl cellulose, sodium polyacrylate, sodium alginate, water-soluble dextran, sodium carboxymethyl starch, pectin, methyl cellulose, ethyl cellulose, xanthan gum, gum arabic, casein, gelatin, agar, diglycerol, propylene glycol, polyethylene glycol, vaseline, paraffin, stearyl alcohol, stearic acid, human serum albumin (HSA), mannitol, sorbitol, lactose, PBS, sodium chloride, sugars, a biodegradable polymer, a serum-free medium, each of which is pharmaceutically acceptable, or an additive which is acceptable as a pharmaceutical additive.

In particular, in the context of the present invention, the pharmaceutical composition preferably contains ammonium sulfate, L-histidine, purified sucrose, sodium hydroxide, hydrochloric acid, or the like.

The container in which a pharmaceutical composition is filled is not particularly limited, and it is preferably made of a material having low oxygen permeability. Examples of the container include a plastic container, a glass container, and a bag made of a laminate film having an aluminum foil, an aluminum-deposited film, an aluminum oxide-deposited film, a silicon oxide-deposited film, a polyvinyl alcohol, an ethylene-vinyl alcohol copolymer, polyethylene terephthalate, polyethylene naphthalate, polyvinylidene chloride, or the like as a gas barrier layer. If necessary, light may be shielded by adopting a bag or the like using a colored glass, an aluminum foil, aluminum-deposited film or the like.

In the container in which a pharmaceutical composition is filled, in order to prevent oxidation by oxygen present in the space in the container, it is preferable to replace gases in the container space and drug solution with inert gases such as nitrogen. For example, an injection solution is bubbled with nitrogen, whereby the filling of the injection solution into a container can be carried out under a nitrogen atmosphere.

The administration method of a pharmaceutical composition is preferably parenteral administration. For example, intravenous injection such as intravenous drip, intramuscular injection, intraperitoneal injection, subcutaneous injection, intraocular injection, or intrathecal injection may be selected. The specific administration method of a liposome composition includes, for example, a syringe, and administration by intravenous drip.

The dose of a drug contained in the pharmaceutical composition is usually selected in the range of 0.01 mg to 100 mg/kg body weight/day. However, the liposome composition of the present invention is not limited to such a dose.

(Release Rate)

The release rate refers to an amount of the drug exiting to the outside of a liposome per unit time. In the present invention, the release rate in blood plasma at 37° C. is preferably 10 mass %/24 hr to 70 mass %/24 hr, more preferably 20 mass %/24 hr to 60 mass %/24 hr, and still more preferably 20 mass %/24 hr to 50 mass %/24 hr.

The release rate is temperature-dependent and is therefore preferably measured under the constant temperature conditions. For example, in the case of a human, the temperature is not particularly limited, but it is preferable to measure the release rate at a temperature in the range of body temperature (35° C. to 38° C.).

In the case where the drug contained in the liposome is an anticancer agent, when the release rate is less than 10 mass %/24 hr, a sufficient exposure time in the body as an anticancer agent cannot be obtained, correspondingly the expected drug efficacy is not achieved in many cases. Further, liposomes containing an anticancer agent remain in the body for an unnecessarily long time in some cases, consequently unexpected toxicity may be expressed due to accumulation thereof in tissues such as skin where such liposomes hardly naturally distribute. Further, when the release rate is greater than 70 mass %/24 hr, since the amount of a drug exposed per unit time is increased, the maximum blood concentration increases, thereby increasing toxicity, and also the leaked drug is distributed in tissues other than the area of tumor or is subjected to rapid metabolism, resulting in decreased retentivity in blood, which is thus unfavorable.

As described above, in the case of obtaining an appropriate release in blood plasma, when release of a drug occurs similarly in a buffer or the like, the drug may be leaked during storage of a formulation, or the drug may be leaked during dilution with an infusion solution upon administration of a formulation. Therefore, it is necessary to inhibit leakage of the drug into physiological saline that does not contain blood plasma components, and the release rate is preferably 10 mass %/24 hr or less.

The drug contained in the liposomes can be measured by a method such as high-performance liquid chromatography or mass spectrometry.

In addition, when measuring the release rate of a drug, the dosage of the drug varies depending on the subject to be administered, target organ, symptoms, the method of administration or the like. For example, in the case of an injection, for example, for a human (a patient; having a body weight of 60 kg), it is preferable to administer a dose of about 0.01 to 30 mg/day, preferably about 0.1 to 20 mg/day, and more preferably about 0.1 to 10 mg/day by intravenous injection. For other animal species, an amount converted in terms of body weight and surface area with respect to the above-specified dose per body weight of 60 kg may be administered.

(Tumor Volume)

In the present invention, a tumor may be transplanted into a model animal (preferably, a mouse or rat) in order to measure a tumor volume. In the case where the liposome composition of the present invention is administered to a subject such as a mammal, the effect of tumor volume growth inhibition can be observed. The inhibition of tumor volume growth is dependent on the drug to be used, a combination of lipids or the like constituting liposomes, and an effective amount. The inhibition of tumor volume growth refers to at least one of tumor growth inhibition, tumor quiescence, and substantial or complete tumor regression.

In the case where the liposome composition of the present invention is administered to a subject such as a mammal, the model animals are assigned into a treatment group and a control group, and tumor cell transplantation can be initiated, for example, after tumor cells were grown to a size of 100 to 1000 $mm^2$ so that the tumor cells settle. A dose of 0.01 to 100 mg/kg may be administered based on the body weight at the initiation of treatment. For example, in the case where the model animal is a mouse, animals were daily weighed as a whole until the mice of each group reach the lowest body weight, as an evaluation of the liposome composition of the present invention. Then, until the end of the experiment, the body weight of animals was measured for each group. The tumor may be measured with a caliper or the like until the final sacrifice is made for the time of sampling, until the tumor reaches 2000 $mm^3$, or until the animals reach to death.

The tumor volume in a mammalian subject may be measured using any method appreciated in the art. For example, the tumor volume can be evaluated according to Equation: $(a \times b^2) \times 0.5$ (where "a" is a maximum diameter, and "b" is a length of the minor axis), using the measurements of a caliper. Further, the tumor volume in a human subject can be evaluated by a technique such as diagnostic imaging, for example computed tomography (CT) scan or magnetic resonance imaging (MRI) scan.

INDUSTRIAL APPLICABILITY

According to the liposome composition and the method for producing the same of the present invention, it is possible to provide a liposome composition which has a practically required long-term preservation stability, and which has a release rate of a drug on the order of several tens of hours due to releasability of a drug being able to be suitably controlled by rendering an inner water phase hyper-osmotic; and a method for producing the same. The liposome composition of the present invention is applicable for pharmaceuticals, cosmetics, foodstuff, or the like, and is particularly useful for pharmaceutical applications.

EXAMPLES

Hereinafter, the present invention will be described in detail with reference to Examples. However, the present invention is not limited to such Examples.

The mixing ratio in the solvent composition refers to a volume ratio. For example, "ethanol/ethyl acetate=90/10" refers to 90% ethanol/10% ethyl acetate by a volume ratio.

The total phase refers to an oil phase and a water phase.

Examples 1 and 2 and Comparative Examples 1 to 3 a) Preparation of Oil Phase 1.79 g of hydrogenated soybean phosphatidylcholine and 0.22 g of cholesterol were taken to be a molar ratio of 76/19, and then 15 ml of an organic solvent (ethanol/ethyl acetate=1/1) was added thereto, followed by warming to 70° C. and dissolving the lipids to prepare an oil phase.

b) Preparation of Water Phase

Gemcitabine hydrochloride was dissolved to 8 mg/mL using water for injection and 10×PBS (pH 7.4) (manufactured by NIPPON GENE CO., LTD.). At this time, the osmotic pressure was adjusted to the value shown in Table below by changing the ratio of water for injection:PBS.

TABLE 1

|  | Comparative Example 1 | Comparative Example 2 | Example 1 | Example 2 | Comparative Example 3 |
| --- | --- | --- | --- | --- | --- |
| Osmotic pressure (mOsm/L) | 126 | 238 | 500 | 619 | 749 | c) Drug-Encapsulating Step Carried Out Simultaneously with Liposome Particle Formation by Emulsification The water phase was warmed to 70° C., the oil phase was added in such a way that a volume ratio of water phase/oil phase=8/3 is achieved, and then two phases were mixed using an emulsification machine (Excel Auto homogenizer ED-3, manufactured by NIHONSEIKI KAISHA LTD.) at 3000 rpm for 10 minutes, followed by mixing at 6000 rpm for 10 minutes and then at 12000 rpm for 10 minutes. Thereafter, 0.41 g of N-(carbonyl-methoxypolyethylene glycol 2000)-1,2-distearoyl-sn-glycero-3-phosphoethanolamine sodium salt (hereinafter, also referred to as DSPE-PEG) was added as an aqueous solution in such a way that a molar ratio of hydrogenated soybean phosphatidylcholine, cholesterol, and DSPE-PEG was to 76/19/5. Subsequently, the organic solvent and water were evaporated by continuous stirring while maintaining the warming at 70° C., and the evaporation was discontinued by stopping warming and stirring at the point of time when reaching the osmotic pressure shown in Table 2. The osmotic pressure at this time becomes an inner water phase osmotic pressure of the drug-encapsulated liposome to be completed. Subsequently, sizing was carried out by sequentially passing the resulting liposome particles through a 0.2 μm filter and a 0.05 μm filter using an extruder (Mini Extruder, manufactured by Avanti Polar Lipids) under the warming of 70° C. to 80° C.

TABLE 2

|  | Comparative Example 1 | Comparative Example 2 | Example 1 | Example 2 | Comparative Example 3 |
| --- | --- | --- | --- | --- | --- |
| Osmotic pressure (mOsm/L) | 309 | 576 | 1101 | 1439 | 1716 |

Completion of Liposome Composition by Dialysis

10×PBS (pH 7.4) (manufactured by NIPPON GENE CO., LTD.) diluted 10-fold (by volume) with water was prepared as a dialysis liquid. The osmotic pressure of this liquid was 307 mOsm/L. This osmotic pressure becomes an outer water phase osmotic pressure of the drug-encapsulated liposome to be completed. Using this dialysis liquid, dialysis was carried out at room temperature to remove unencapsulated gemcitabine hydrochloride and individual solutes present in the outer water phase of the drug-loading liquid, and the outer water phase was replaced with the dialysis liquid.

Measurement of Volume Average Particle Size

The volume average particle size of a sample diluted 1000-fold (by weight) with water was measured by a dynamic light scattering method using a nano track UPA-UT (manufactured by Nikkiso Co., Ltd.). The results are shown in Table 3.

Measurement of Release Rate in Blood Plasma

50 μL of each of the liposome compositions of Examples 1 and 2 and Comparative Examples 1 to 3 was diluted 20-fold (by volume) with the mouse blood plasma, and incubated at 37° C. for 24 hours, followed by collecting 100 μL at 0, 1, 4, 9, and 24 hours. Subsequently, centrifugal filtration was carried out under the conditions of 7400×g, 30 minutes, and 4° C., using an ultrafiltration filter (Amicon Ultra-0.5 10 kDa, manufactured by Millipore Corporation). The amount of drug contained in the recovered filtrate was quantified by HPLC, and the release rate and the outer water phase percentage were calculated by the following equation.

Release rate (%/24 hr)=(amount of drug in filtrate after 24 hour incubation−amount of drug in filtrate before incubation)×20/amount of drug contained in total phase of liposome composition×100   Equation:

Outer water phase percentage (%)=(drug concentration in filtrate×10)/drug concentration in formulation×100   Equation:

The results are shown in Table 3 and FIG. 1.

TABLE 3

|  | Comparative Example 1 | Comparative Example 2 | Example 1 | Example 2 | Comparative Example 3 |
| --- | --- | --- | --- | --- | --- |
| Gemcitabine concentration (mg/mL) | 1.8 | 1.26 | 1.41 | 1.23 | 0.80 |
| Volume average particle size (nm) | 69.3 | 65.4 | 72.8 | 76.0 | 70.0 |
| Inner water phase/outer water phase osmotic pressure ratio | 1.0 | 1.9 | 3.6 | 4.7 | 5.6 |
| Release rate (%/24 hr) | 5.0 | 7.5 | 28.6 | 57.3 | 94.7 |

From the above-described results, it can be seen that the present invention enables the release rate in blood plasma to be optionally controlled by adjusting the osmotic pressure of the inner water phase to the outer water phase.

Example 3 a) Preparation of Oil Phase 16.6 g of hydrogenated soybean phosphatidylcholine, 2.0 g of cholesterol and 4.3 g of DSPE-PEG were taken to be a molar ratio of 76/19/5, and then 405 mL of an organic solvent (ethanol/ethyl acetate=75/25) was added thereto, followed by warming to 70° C. and dissolving the lipids to prepare an oil phase.

b) Preparation of Water Phase 6 mM phosphate buffer (pH 7.86) was prepared to serve as a water phase.

c) Preparation of Drug-Unencapsulated Liposome

The water phase was warmed to 70° C., the oil phase was added in such a way that a volume ratio of water phase/oil phase=8/3 is achieved, and then two phases were mixed using a rotary agitation type emulsification machine at circumferential speed of 20 m/s and 13000 rpm for 30 minutes. Thereafter, the organic solvent and water were evaporated by blowing with nitrogen while warming to a temperature higher than or equal to the phase transition temperature, thereby concentrating the mixture to an about 1/10 volume relative to the volume before emulsification, thus obtaining a drug-unencapsulated liposome. The particle size at this time was 67.0 nm.

d) Preparation of Drug-Encapsulated Liposome

Drug Loading
1) Preparation of PBS (10×)
81.63 g of sodium chloride, 29.01 g of disodium hydrogen phosphate 12 hydrate, and 2.29 g of sodium dihydrogen phosphate dihydrate were dissolved in 948 g of water for injection to prepare PBS (10×). The PBS prepared here was used in Example 3.
2) Preparation of Drug-Loading Liquid
7.68 g of gemcitabine hydrochloride, 31.99 g of PBS (10×), 44.83 g of Japanese Pharmacopoeia water for injection, and 1.60 mL of 8N sodium hydroxide were mixed to prepare a drug solution. Subsequently, 17.64 mL of the drug solution, 18.00 mL of drug-unencapsulated liposomes, and 0.36 mL of 8N sodium hydroxide were mixed in each of four vials. The mixture was heated at 70° C. for 10 minutes and then allowed to cool at 40° C. for 30 minutes. The osmotic pressure of this liquid is 1039 mOsm/L which becomes an inner water phase osmotic pressure of the liposome composition to be completed. Then, this liquid was diluted with 2.7-fold diluted PBS (10×). The liquid was pooled in one vial and used as a drug-loading liquid.

Completion of Liposome Composition by Dialysis
A 275 mM sucrose/10 mM histidine aqueous solution was prepared as a dialysis liquid. The osmotic pressure of this liquid was 285 mOsm/L. Using this dialysis liquid, dialysis was carried out at room temperature to remove unencapsulated gemcitabine hydrochloride and individual solutes present in the outer water phase of the drug-loading liquid, and the outer water phase was replaced with the dialysis liquid. From the above-described steps, a drug-encapsulated liposome composition having a gemcitabine concentration of 0.68 mg/mL, a particle size of 73 nm, and an inner water phase/outer water phase osmotic pressure ratio of 3.6-fold was obtained.

Measurement of Release Rate in Blood Plasma and Outer Water Phase Percentage

50 µL of the liposome composition obtained in Example 3 was diluted 20-fold (by volume) with a solution which had been diluted with PBS (manufactured by Gibco, Life Technology) such that the mouse blood plasma is 0%, 1%, 3%, 10%, 33%, and 100%, respectively, and incubated at 37° C. for 24 hours, followed by collecting 100 µL at 0, 1, 4, 9, and 24 hours. Subsequently, centrifugal filtration was carried out under the conditions of 7400×g, 30 minutes, and 4° C., using an ultrafiltration filter (Amicon Ultra-0.5 10 kDa, manufactured by Millipore Corporation). The amount of drug contained in the recovered filtrate was quantified by HPLC, and the release rate and the outer water phase percentage were calculated by the following equation.

Figure 2:
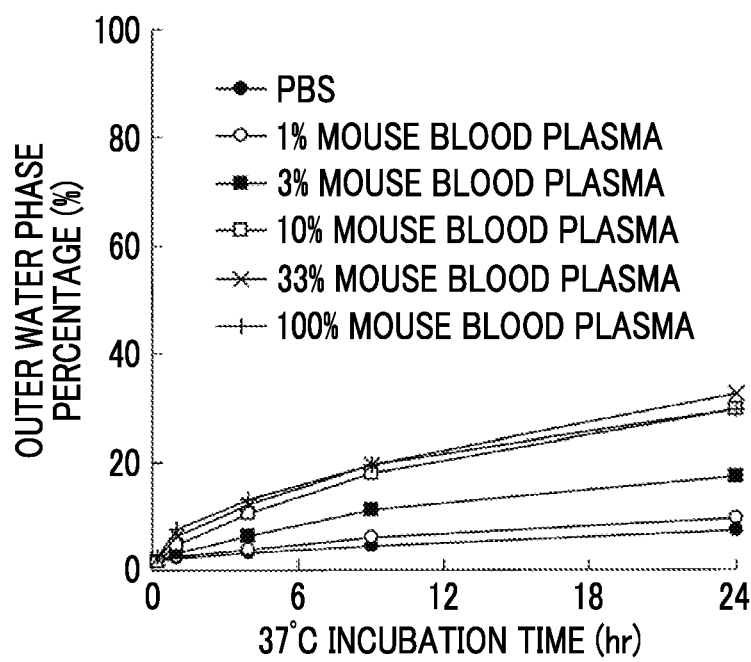
FIG. 2 is a plot of a relationship between the incubation time and a release rate.

Release rate (%/24 hr)=(amount of drug in filtrate after 24 hour incubation−amount of drug in filtrate before incubation)×20/amount of drug contained in total phase of liposome composition×100  Equation:

Outer water phase percentage (%)=(amount of drug in filtrate at each incubation time point−amount of drug in filtrate before incubation)×20/amount of drug contained in total phase of liposome composition×100  Equation:

The results are shown in Table 4 and FIG. 2.

TABLE 4

| | Mouse blood plasma concentration (%) | | | | | |
|---|---|---|---|---|---|---|
| | 0 | 1 | 3 | 10 | 33 | 100 |
| Release rate (%/24 hr) | 8 | 13 | 27 | 34 | 32 | 30 |

From the results in Table 4, it was found that the liposome composition of the present invention exhibits suppressed release in PBS and surprisingly accelerated release in blood plasma. This phenomenon does not occur in a liposome composition where an osmotic pressure difference of an inner water phase to an outer water phase is not large as can be seen from the results of a release test in blood plasma of Comparative Examples 1 and 2. An improvement of the release only in blood plasma results in facilitated release only when administered into the body while suppressing leakage during storage or dilution into an infusion of a liposome composition, which is significantly advantageous in practical use. It is believed that when the osmotic pressure of the inner water phase is high, the lipid membrane changes into an interdigitated gel structure, thus resulting in enhanced interaction with lipoproteins or the like contained in blood plasma, and consequently the releases is promoted.

Example 4

The liposome composition of Example 4 was prepared in the same manner as in Example 3, except that a drug-loading liquid was prepared by a method described below.
Preparation of Drug-Loading Liquid
1.03 g of gemcitabine hydrochloride, 17.92 g of 10×PBS (manufactured by Gibco, Life Technology), 10.76 g of Japanese Pharmacopoeia water for injection, and 3.42 mL of IM sodium hydroxide were mixed to prepare a drug solution. Subsequently, 27.0 mL of the drug solution, and 27.0 mL of the drug-unencapsulated liposome were mixed. The mixture was heated at 70° C. for 10 minutes and then allowed to cool at room temperature for 30 minutes to prepare a drug-loading liquid. The osmotic pressure of this liquid was 1014 mOsm/L.

Comparative Examples 4 and 5

The liposome composition of Comparative Example 4 was prepared in the same manner as in Example 4, except that an amount of Japanese Pharmacopoeia water for injection was increased for a reduced amount of 10×PBS (manufactured by Gibco, Life Technology), and the osmotic pressure was adjusted to 239 mOsm/L.
The liposome composition of Comparative Example 5 was prepared in the same manner as in Example 4, except that an amount of Japanese Pharmacopoeia water for injection was decreased for an increased amount of 10×PBS (manufactured by Gibco, Life Technology), and the osmotic pressure was adjusted to 1482 mOsm/L.

Measurement of Average Particle Size

The average particle size was determined by measuring a cumulant average particle size of a sample diluted 100-fold (by weight) with 1×PBS (manufactured by Gibco, Life Technology) by a dynamic light scattering method using a FPAR-100AS (Otsuka Electronics Co., Ltd.). The results are shown in Table 5.

Measurement of Release Rate in Blood Plasma

50 µL of each of the liposome compositions obtained in Example 4 and Comparative Examples 4 and 5 was diluted 20-fold (by volume) with the mouse blood plasma, and incubated at 37° C. for 24 hours, followed by centrifugal filtration using an ultrafiltration filter (Amicon Ultra-0.5 10 kDa, manufactured by Merck Millipore Corporation) under the conditions of 7400×g, 30 minutes, and 4° C. The amount of drug contained in the recovered filtrate was quantified by HPLC, and the release rate was calculated by the following equation.

Release rate (%/24 hr)=(amount of drug in filtrate after 24 hour incubation−amount of drug in filtrate before incubation)×20/amount of drug contained in inner water phase of liposome composition×100     Equation:

The results are shown in Table 5.

TABLE 5

|  | Comparative Example 4 | Example 4 | Comparative Example 5 |
|---|---|---|---|
| Gemcitabine concentration (mg/mL) | 1.14 | 0.85 | 0.61 |
| Average particle size (nm) | 71 | 74 | 80 |
| Inner water phase/outer water phase osmotic pressure ratio | 0.84 | 3.6 | 5.2 |
| Release rate (%/24 hr) | 8 | 34 | 90 |

Figure 3:
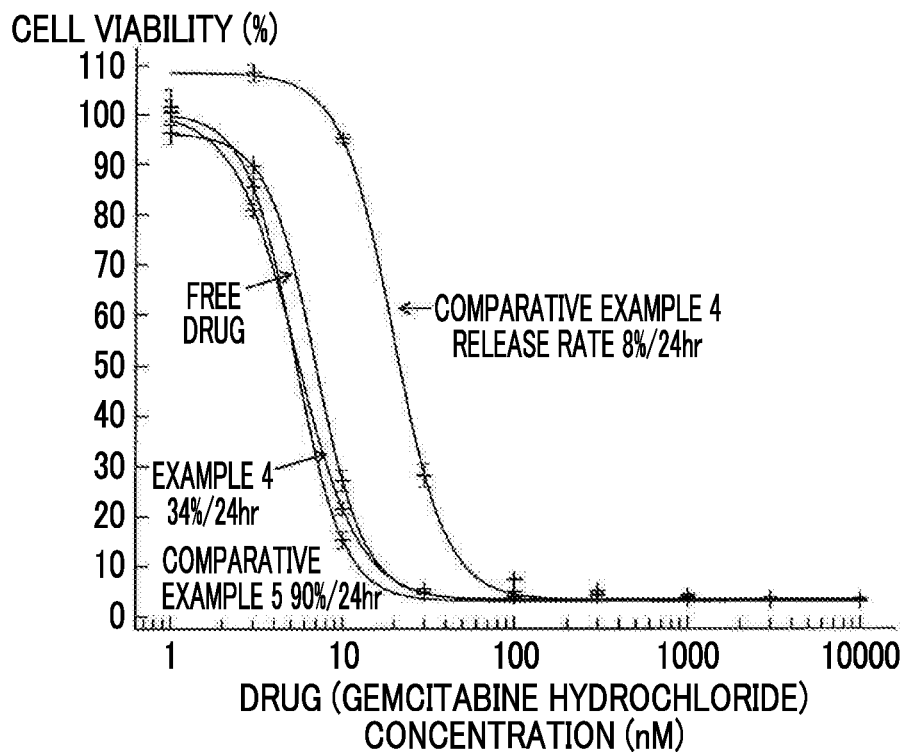
FIG. 3 is a plot of a relationship between a drug concentration of gemcitabine hydrochloride and cell viability.

In Vitro Cancer Cell Growth Inhibition $2×10^3$ cells/mL/well of Capan-1 (human pancreatic cancer cell line) were seeded onto a 96-well plate. Subsequently, a free drug (gemcitabine hydrochloride) solution, and a drug encapsulated in the liposome compositions of Example 4 and Comparative Examples 4 and 5 were added at each concentration, and cultured until after 144 hours. The cell viability was calculated from the amount of luminescence obtained by a Luminescent Cell Viability Assay after the completion of the culture. The results are shown in FIG. 3. In addition, a drug effect concentration (IC50) that inhibits 50% of cancer cell growth was determined. The free drug exhibited an IC50 of 7 nM, the liposome composition of Example 4 exhibited an IC50 of 6 nM, Comparative Example 4 exhibited an IC50 of 22 nM, and Comparative Example 5 exhibited an IC50 of 5 nM. It can be seen from FIG. 3 that the efficacy in the liposome composition of Comparative Example 4 having a low release rate is significantly reduced.

Measurement of Retentivity in Blood

Figure 4:
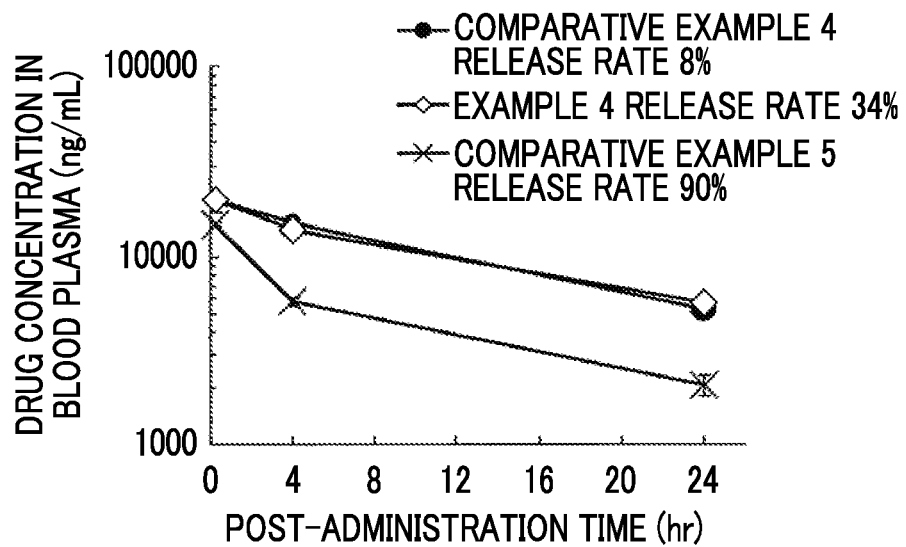
FIG. 4 is a plot of a relationship between a post-administration time and a free gemcitabine concentration in blood plasma.

The liposome compositions of Example 4 and Comparative Examples 4 and 5 at a dose of 1 mg/kg in terms of drug amount were administered via tail vein injection to 7-week old male BALB/c mice under ad libitum feeding conditions. Blood was collected at 15 minutes, 4 hours, and 24 hours after the administration was completed, and centrifuged to quantify a free gemcitabine concentration in blood plasma. The results are shown in FIG. 4. Further, a plasma half-life (hereinafter, also referred to as Tin) was determined. The liposome composition of Example 4 exhibited a $T_{1/2}$ of 15 hr, Comparative Example 4 exhibited a $T_{1/2}$ of 13 hr, and Comparative Example 5 exhibited a $T_{1/2}$ of 13 hr. Although the $T_{1/2}$ of free gemcitabine in mice is 0.7 hr and any of the liposome compositions exhibited significantly improved retentivity in blood, it was found that Comparative Example 4 having a release rate of 90% hr has relatively poor retentivity. This indicates that the concentration is decreased when leakage in blood is excessive because the drug is rapidly metabolized.

Examples 5 and 6 and Comparative Example 6

The liposome composition of Example 5 was prepared in the same manner as in Example 3, except that the scale of a drug-loading liquid was different. The liposome composition of Example 6 was prepared in the same manner as in Example 3, except that an amount of water for injection corresponding to an increased amount of PBS (10×) prepared in d) 1) of Example 3 was decreased for controlling an osmotic pressure, and the liposome composition of Comparative Example 6 was prepared in the same manner as in Example 3, except that an amount of water for injection corresponding to a further increased amount of PBS (10×) prepared in d) 1) of Example 3 was decreased.

The release rate was measured in the same manner as in Example 4.

The average particle size was determined by measuring a cumulant average particle size of a sample diluted 33-fold (by weight) with 1×PBS (manufactured by Gibco, Life Technology) by a dynamic light scattering method using a FPAR-100AS (Otsuka Electronics Co., Ltd.).

The results are shown in Table 6.

TABLE 6

|  | Example 5 | Example 6 | Comparative Example 6 |
|---|---|---|---|
| Gemcitabine concentration (mg/mL) | 0.67 | 0.66 | 0.60 |
| Average particle size (nm) | 73 | 73 | 74 |
| Inner water phase/outer water phase osmotic pressure ratio | 3.6 | 4.0 | 4.6 |
| Release rate (%/24 hr) | 32 | 48 | 88 |

Drug Efficacy Testing in Subcutaneously Transplanted Tumor-Bearing Mouse Model of Capan-1

Figure 5:
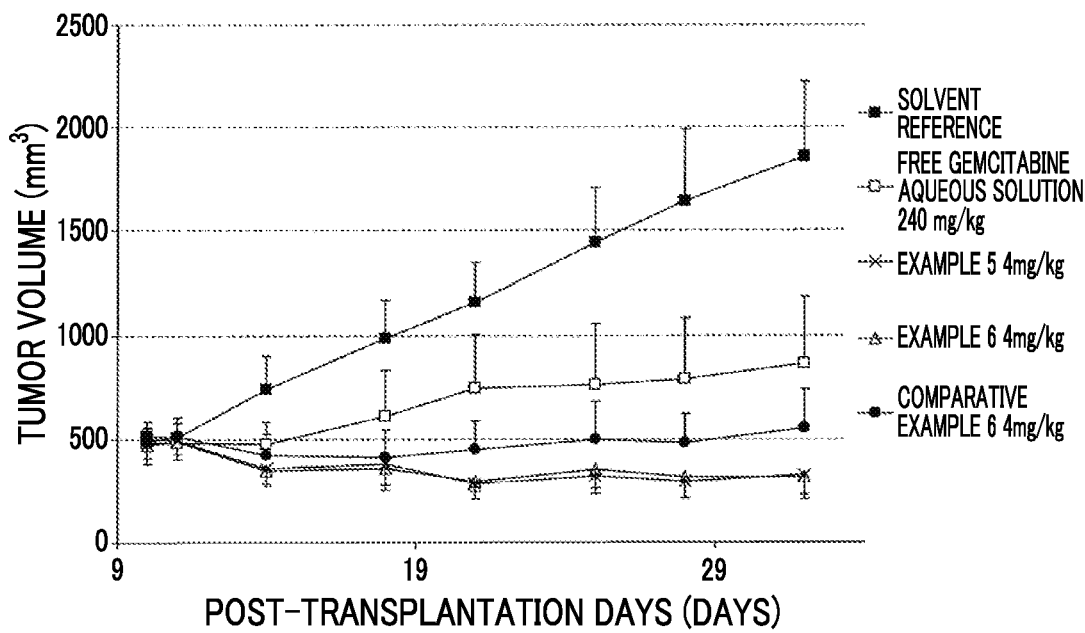
FIG. 5 is a plot of a relationship between a tumor volume and post-transplantation days when Capan-1 cells are transplanted in a mouse to form a subcutaneous tumor.
Figure 6:
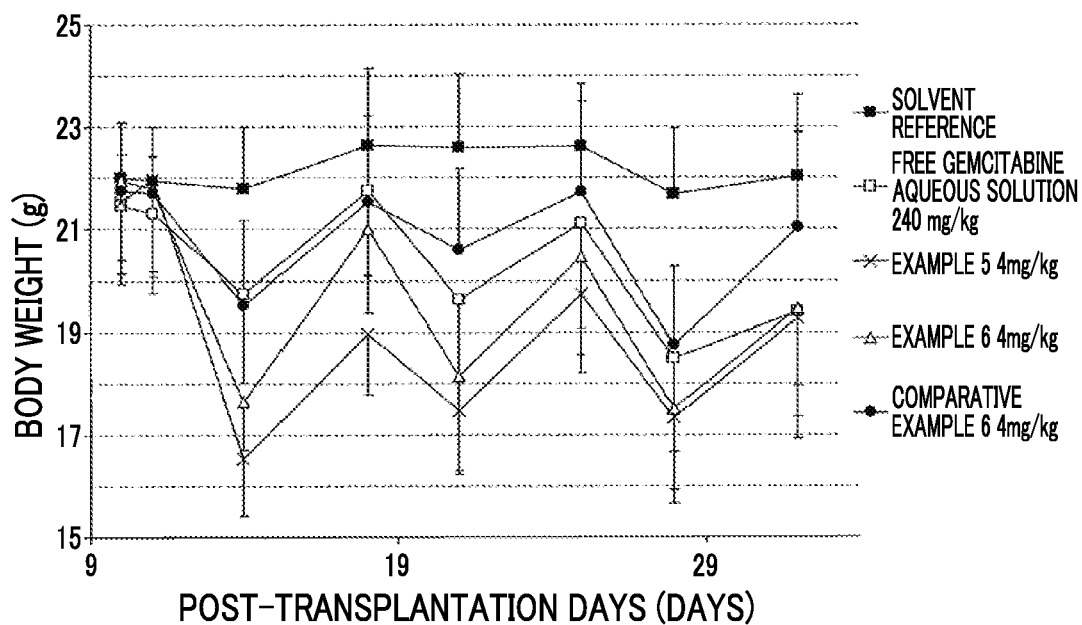
FIG. 6 is a plot of a relationship between a mouse body weight and post-transplantation days when Capan-1 cells are transplanted in a mouse to form a subcutaneous tumor.

$1×10^7$ cells of Capan-1 which is a human pancreatic cancer cell line were transplanted under the skin of the flank of female nude mice to form a subcutaneous tumor. From post-transplantation day 11, administration of a free gemcitabine aqueous solution (240 mg/10 mL/kg/week), liposome compositions (4 mg/10 mL/kg/week) of Examples 5 and 6 and Comparative Example 6, and a solvent reference (9.4% sucrose) was initiated. The free gemcitabine aqueous solution, the liposome compositions and the solvent reference were administered by tail vein injection. Taking once a week as one course, a total of 3 courses were carried out. A tumor volume on post-transplantation day 32 was measured with a caliper, and inhibitory effects on subcutaneous tumor were evaluated. The results are shown in FIG. 5. Further, variability in body weight was measured as a measure of toxicity. The results are shown in FIG. 6.

When compared with free gemcitabine, all the liposome compositions of Examples 5 and 6 and Comparative Example 6 were found to have tumor inhibitory effects, since the tumor inhibition rate was significantly improved in the administration groups of Examples 5 and 6 and Comparative Example 6 despite the weight loss rate reflecting toxicity was equivalent to free gemcitabine. Further, it was found that the liposome compositions of Examples 5 and 6 also surprisingly exhibited the regression of tumor, thus showing high effects. On the other hand, it was found that the liposome composition of Comparative Example 6 having a high release rate in blood did not exhibit tumor regression effects and therefore did not have an optimal release rate.

Example 7

The liposome composition of Example 7 was prepared in the same manner as in Example 3, except that the preparation of a drug-loading liquid described below was different.

Preparation of Drug-Loading Liquid 1.02 g of gemcitabine hydrochloride, 17.82 g of 10×PBS (manufactured by Gibco, Life Technology), 10.76 g of Japanese Pharmacopoeia water for injection, and 3.42 mL of 1M sodium hydroxide were mixed to prepare a drug solution. Subsequently, 27.00 mL of the drug solution, 27.00 mL of drug-unencapsulated liposomes, and 3.42 mL of 1M sodium hydroxide were added and mixed in a vial. The mixture was heated at 70° C. for 10 minutes and then allowed to cool at 40° C. for 30 minutes. This liquid was served as a drug-loading liquid. The osmotic pressure of this liquid is 1084 mOsm/L which becomes an inner water phase osmotic pressure of the liposome composition to be completed.

The release rate was measured in the same manner as in Example 4.

The average particle size was determined by measuring a cumulant average particle size of a sample diluted 100-fold (by weight) with 1×PBS (manufactured by Gibco, Life Technology) by a dynamic light scattering method using a FPAR-100AS (Otsuka Electronics Co., Ltd.).

The results are shown in Table 7.

TABLE 7

|  | Example 7 |
| --- | --- |
| Gemcitabine concentration (mg/mL) | 0.85 |
| Average particle size (nm) | 74.0 |
| Inner water phase/outer water phase osmotic pressure ratio | 3.8 |
| Release rate (%/24 hr) | 34 |

Drug Efficacy Testing in Subcutaneously Transplanted Tumor-Bearing Mouse Model of BxPC-3

This is a test confirming the effect on cancer cells that show low in vivo sensitivity to free gemcitabine.

Figure 7:
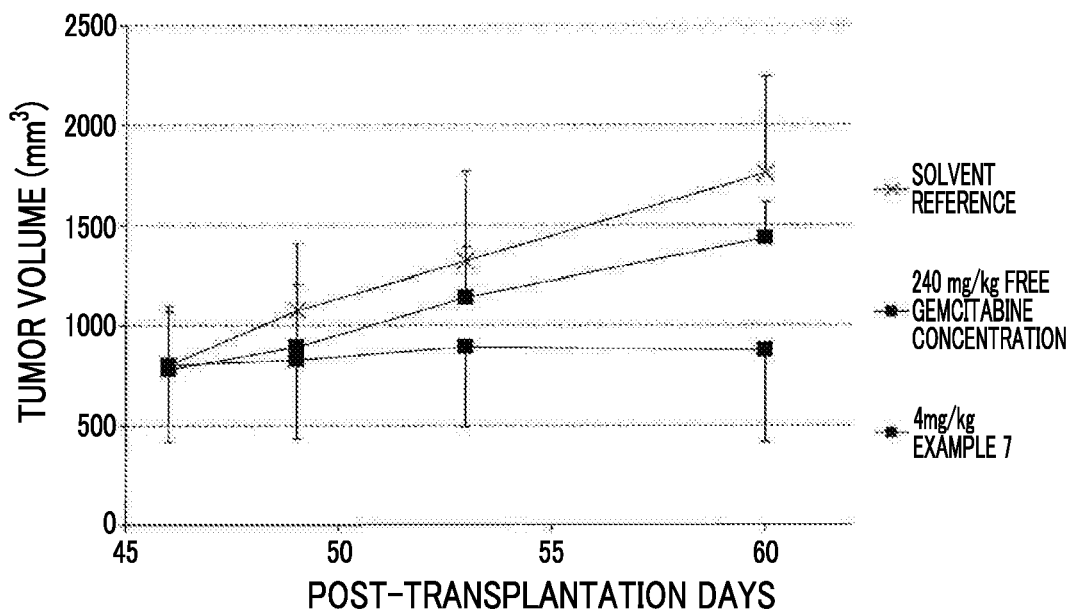
FIG. 7 is a plot of a relationship between post-transplantation days and the tumor volume when BxPC-3 cells are transplanted in a mouse to form a subcutaneous tumor.
Figure 8:
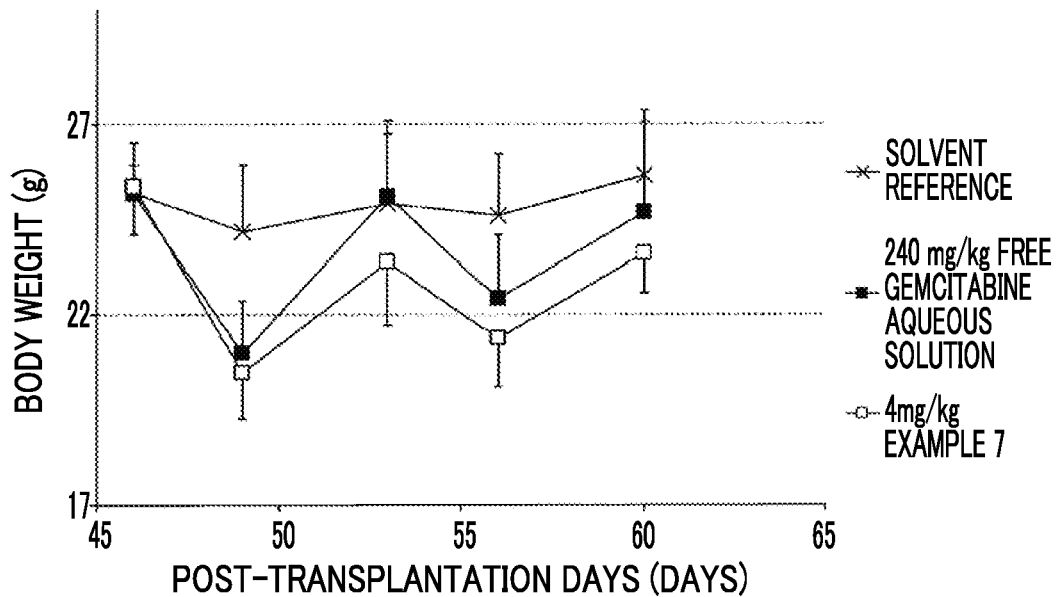
FIG. 8 is a plot of a relationship between post-transplantation days and the mouse body weight when BxPC-3 cells are transplanted in a mouse to form a subcutaneous tumor.

5×10$^6$ cells of BxPC-3 which is a human pancreatic cancer cell line that becomes low-sensitive in vivo to free gemcitabine were transplanted under the skin of the flank of female nude mice to form a subcutaneous tumor. From post-transplantation day 46, administration of a free gemcitabine aqueous solution (240 mg/10 mL/kg/week) and liposome compositions of Examples 6 to 9 (4 mg/10 mL/kg/week) was initiated. The free gemcitabine aqueous solution was administered by intraperitoneal injection, and the liposome compositions and the solvent reference (9.4% of sucrose) were administered by tail vein injection. Taking once a week as one course, a total of 2 courses were carried out. The tumor volume on post-transplantation day 60 was measured with a caliper, and inhibitory effects on subcutaneous tumor were evaluated. The results are shown in FIG. 7. Further, variability in body weight was measured as a measure of toxicity. The results are shown in FIG. 8.

When compared with free gemcitabine, the liposome composition of Example 7 was surprisingly found to have high tumor inhibitory effects also for a cell line having low sensitivity to free gemcitabine, since the tumor inhibition was significantly improved in the administration group of Example 7 despite the weight loss reflecting toxicity was equivalent to free gemcitabine.

Example 8

The liposome composition of Example 8 was prepared in the same manner as in Example 3, except that the scale of a drug-loading liquid was different.

The release rate was measured in the same manner as in Example 4.

The average particle size was determined by measuring a cumulant average particle size of a sample diluted 33-fold (by weight) with 1×PBS (manufactured by Gibco, Life Technology) by a dynamic light scattering method using a FPAR-100AS (Otsuka Electronics Co., Ltd.).

The results are shown in Table 8.

TABLE 8

|  | Example 8 |
| --- | --- |
| Gemcitabine concentration (mg/mL) | 0.62 |
| Average particle size (nm) | 73 |
| Inner water phase/outer water phase osmotic pressure ratio | 3.6 |
| Release rate (%/24 hr) | 28 |

Figure 9:
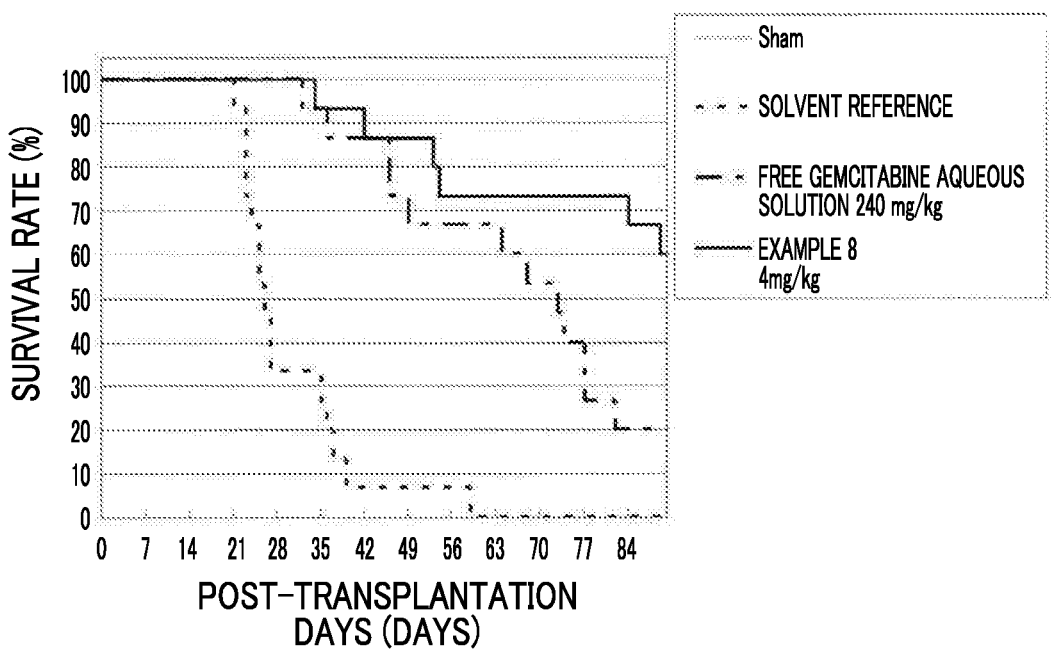
FIG. 9 is a plot of a relationship between post-transplantation days and a survival rate when SUIT-2 cells are transplanted in a mouse to form a tumor.

Drug Efficiency Testing in Mouse Model with Transplantation of SUIT-2 Cells in Pancreas 1×10$^6$ cells of SUIT-2 which is a human pancreatic cancer cell line were transplanted in the pancreas of female nude mice to form a tumor. The reference group with no transplantation of cancer cells but subjected to the same laparotomy was served as a sham group. From post-transplantation day 7 on which metastasis and peritoneal dissemination were observed, a free gemcitabine aqueous solution (240 mg/10 mL/kg), a liposome composition of Example 8 (4 mg/10 mL/kg), and a solvent reference (9.4% sucrose) were administered by tail vein injection to determine a survival curve until post-transplantation day 91. The results are shown in FIG. 9.

It was found that the survival duration was significantly improved in the administration group of Example 8, when compared with free gemcitabine.

Example 9

The liposome composition of Example 9 was prepared in the same manner as in Example 3, except that 10×PBS (manufactured by Gibco, Life Technology) was used instead of PBS (10×) prepared in d) 1) of Example 3, the inner water phase osmotic pressure was different, and the scale of a drug-loading liquid was different, whereby a drug-encapsulated liposome composition having a gemcitabine concentration of 0.71 mg/mL, a particle size of 84 nm, a drug unencapsulation rate of 2.1%, an inner water phase osmotic pressure of 940 mOsm/L, and an outer water phase osmotic pressure of 285 mOsm/L, with an osmotic pressure of an inner water phase relative to that of an outer water phase being 3.3-fold higher was obtained.

Measurement of Preservation Stability

The drug-encapsulated liposomes of Example 9 were filled in a 2 mL vial and stored at 5° C. At a certain point of time, a sample was partially sampled. Using this sample, various evaluations given below were carried out, and the stability of the liposome composition according to the present invention was measured.

Measurement of Stability of Drug

Figure 10:
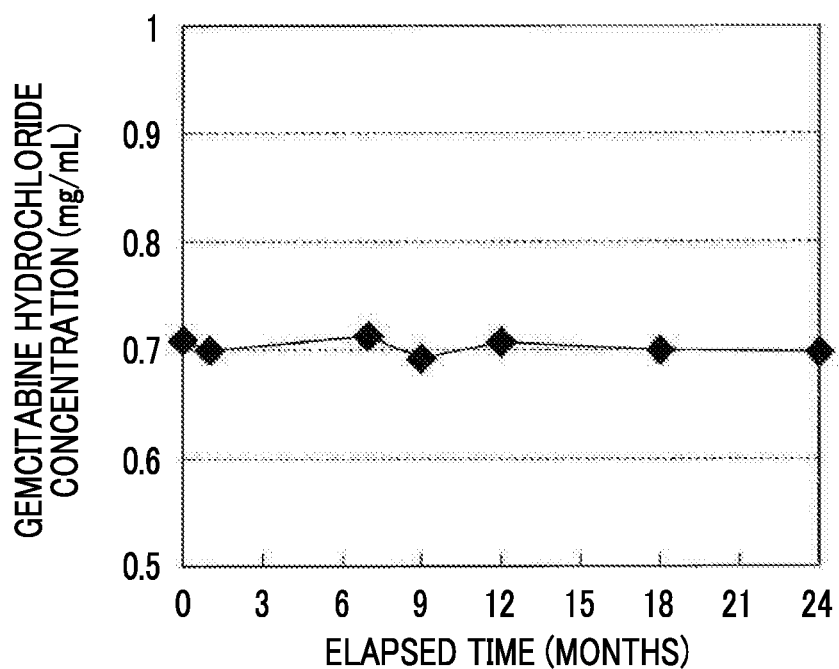
FIG. 10 is a plot of a relationship between an elapsed time and the drug concentration of gemcitabine hydrochloride in the liposome composition of the present invention.

50 µL of the sampled samples was diluted 20-fold (by volume) with methanol to extract the drug encapsulated in a liposome. Subsequently, the extract was diluted 10-fold (by volume) with water, and the amount of drug contained in this liquid was quantified by HPLC. The results are shown in FIG. 10. Over an extended period of 24 months, the drug in the liposome composition of the present invention was found to be sufficiently stable.

Measurement of Unencapsulation Rate

50 µL of the sampled sample was diluted 10-fold (by volume) with water, and subjected to centrifugal filtration using an ultrafiltration filter (Amicon Ultra-0.5 10 kDa manufactured by Millipore Corporation) under the conditions of 7400×g, 30 minutes and 4° C. The amount of drug contained in the recovered filtrate was quantified by HPLC, and the abundance ratio (unencapsulation rate) of the drug present in the outer water phase was calculated by the following equation.

Figure 11:
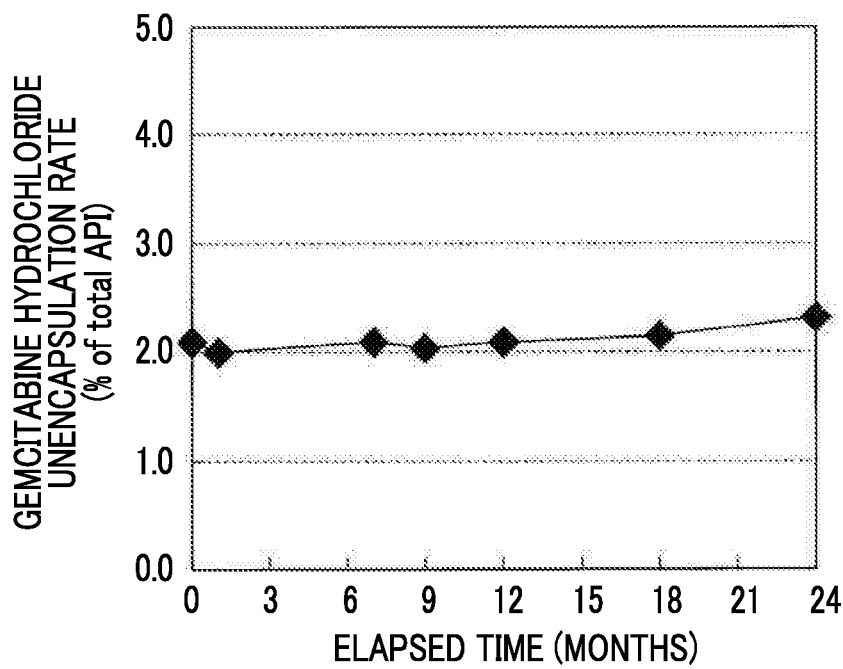
FIG. 11 is a plot of a relationship between the elapsed time and an abundance ratio (unencapsulation rate) of gemcitabine hydrochloride in the liposome composition of the present invention.

Unencapsulation rate (%)=(drug concentration in filtrate×10)/drug concentration in formulation× 100    Equation:

The results are shown in FIG. 11.

Surprisingly, since there was almost no change in the unencapsulation rate over an extended period of 24 months, the drug of the liposome composition of the present invention was found to be sufficiently stable without leaking into the outer water phase.

Measurement of Particle Size

Figure 12:
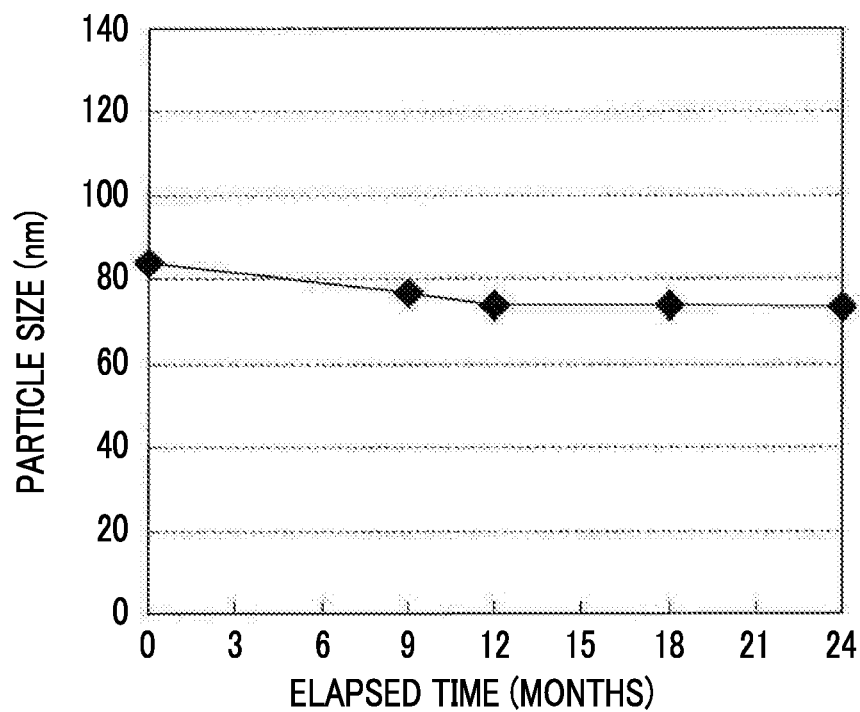
FIG. 12 is a plot of a relationship between the elapsed time and a liposome particle size in the liposome composition of the present invention.

The sampled sample was diluted 33-fold (by volume) with 1×PBS (manufactured by Gibco, Life Technology), and the volume average particle size was measured by a dynamic light scattering method using a FPAR-1000AS (manufactured by Otsuka Electronics Co., Ltd.). The results are shown in FIG. 12. Since there was almost no change in the particle size over an extended period of 12 months, the particles of the liposome composition of the present invention were found to be sufficiently stable.

Measurement of Drug Release Rate in Blood Plasma

50 µL of the sampled sample was diluted 20-fold with the mouse blood plasma, and incubated at 37° C. for 24 hours. Then, centrifugal filtration was carried out using an ultrafiltration filter (Amicon Ultra-0.5 10 kDa manufactured by Millipore Corporation) under the conditions of 7400×g, 30 minutes, and 4° C. The amount of drug contained in the recovered filtrate was quantified by HPLC, and the release rate of the drug released into blood plasma was calculated by the following equation.

Figure 13:
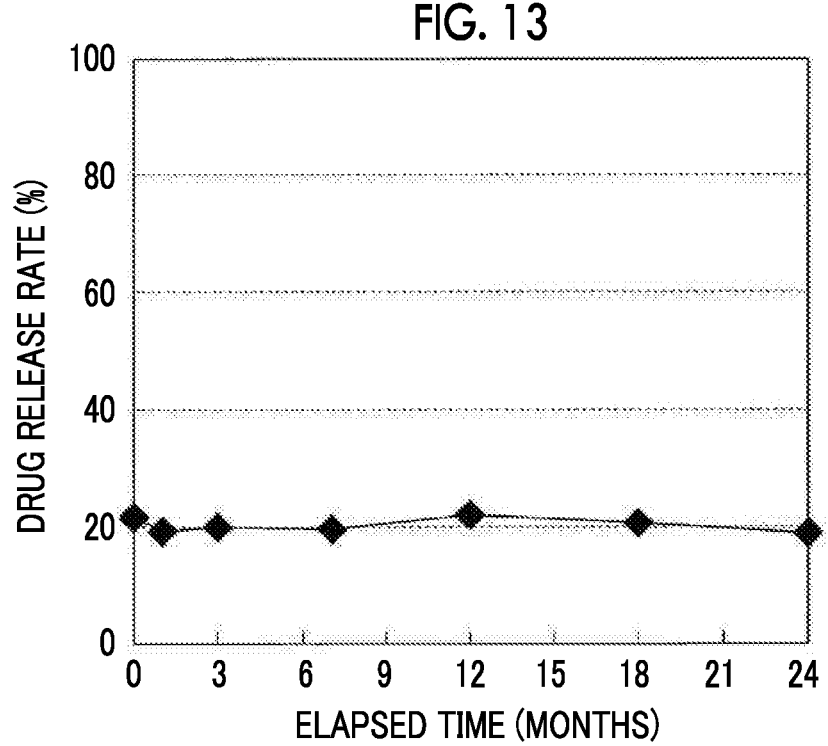
FIG. 13 is a plot of a relationship between the elapsed time and a release rate of the drug released into blood plasma in the liposome composition of the present invention.

Drug release rate (%)=(drug concentration in filtrate×20)/drug concentration in formulation×100    Equation:

The results are shown in FIG. 13.

Surprisingly, it was found that there was almost no change in the drug release rate over an extended period of 12 months.

Example 10

The liposome composition of Example 10 was prepared in the same manner as in Example 3, except for a drug loading step. For the drug loading, 1.9 g of pemetrexed disodium heptahydrate, 2.4 g of sodium chloride, and 24 g of water for injection were mixed, and then dissolved by heating at 45° C. to prepare a drug solution. Subsequently, 8.0 mL of the drug solution and 8.0 mL of the drug-unencapsulated liposomes were mixed and heated at 70° C. for 10 minutes to prepare a drug loading liquid. This liquid was dialyzed to complete a liposome composition.

A drug-encapsulated liposome composition having a pemetrexed concentration of 0.65 mg/mL, a particle size of 76.8 nm, an inner water phase osmotic pressure of 1850 mOsm/L, and an outer water phase osmotic pressure of 285 mOsm/L, with an osmotic pressure of an inner water phase relative to that of an outer water phase being 6.5-fold higher was obtained. The release rate in blood plasma was 29%.

Figure 14:
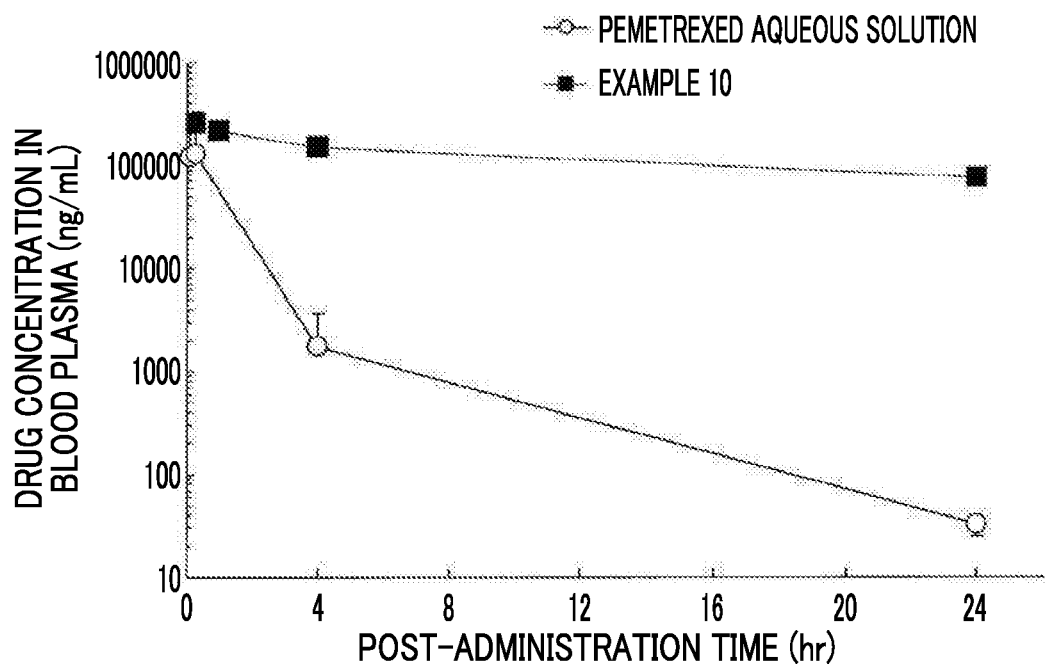
FIG. 14 is a plot of a relationship between the post-administration time and the drug concentration in blood plasma in the liposome composition of the present invention.

Further, the liposome composition of Example 10 at a dose of 6 mg/kg in terms of drug amount was administered via tail vein injection to 8-week old male C3H mice under the non-fasting conditions. Blood was collected at 15 minutes, 1 hour, 4 hours, and 24 hours after the administration was completed, and the free pemetrexed concentration in blood plasma was quantified to calculate a $T_{1/2}$. The results are shown in FIG. 14. The Tin in the case of the drug aqueous solution was 2 hours, whereas the $T_{1/2}$ in the liposome composition of Example 10 was 17 hours which is sufficiently long when compared with the drug aqueous solution, so the DDS formulation was confirmed to exhibit sufficiently long retentivity in blood.

TABLE 9

|  | Osmotic pressure ratio | Release rate (%/24 hr) | In vitro test | In vivo test | Preservative property |
|---|---|---|---|---|---|
| Comparative Example 1 | 1.0 | 5 | — | — | — |
| Comparative Example 2 | 1.9 | 8 | — | — | — |
| Example 1 | 3.6 | 29 | — | — | — |
| Example 2 | 4.7 | 57 | — | — | — |
| Comparative Example 3 | 5.6 | 95 | — | — | — |
| Example 3 | 3.6 | 30 | Decreased release in buffer where blood plasma components are less than 10% | — | — |
| Comparative Example 4 | 0.8 | 8 | Poor cancer cell growth inhibitory efficiency | Excellent retentivity in blood | — |

TABLE 9-continued

| | Osmotic pressure ratio | Release rate (%/24 hr) | In vitro test | In vivo test | Preservative property |
|---|---|---|---|---|---|
| Example 4 | 3.6 | 34 | Good cancer cell growth inhibitory activity | Excellent retentivity in blood | — |
| Comparative Example 5 | 5.2 | 90 | Good cancer cell growth inhibitory activity | Poor retentivity in blood | — |
| Example 5 | 3.6 | 32 | — | Tumor regression effects in Capan-1 subcutaneously transplanted model | — |
| Example 6 | 4.0 | 48 | — | The same as in Example 5 | — |
| Comparative Example 6 | 4.6 | 88 | — | Relatively poor anti-tumor effects | — |
| Example 7 | 3.8 | 34 | — | Having tumor growth inhibitory effects in subcutaneous transplantation model of resistance strain BxPC-3 | — |
| Example 8 | 3.6 | 28 | — | Having OS-prolonging effects in orthotopic transplantation (having metastasis and dissemination) model of SUIT-2 pancreatic cancer cells | — |
| Example 9 | 3.3 | 22 | — | — | Stable over 2 years |
| Example 10 | 6.5 | 29 | — | Excellent retentivity in blood | — |

Table 9 shows osmotic pressure ratios, release rates, in vitro tests, and in vivo tests relating to the liposome compositions of the present invention. From the results shown in Table 9, it was found that a liposome composition, in which a liposome encapsulates a drug in a dissolved state, an osmotic pressure of an inner water phase is 2-fold to 8-fold relative to the osmotic pressure of an outer water phase, and also a release rate of the drug from the liposome is 10%/24 hr to 70%/24 hr in blood plasma at 37° C., has good cancer cell growth inhibitory activity and also excellent retentivity in blood.

What is claimed is:

1. A liposome composition, comprising:
   liposomes each of which has an inner water phase and an aqueous solution which constitutes an outer water phase and in which the liposomes are dispersed,
   wherein each of the liposomes encapsulates a drug in a dissolved state, the osmotic pressure of the inner water phase is 3-fold to 5-fold relative to the osmotic pressure of the outer water phase,
   the release rate of the drug from each of the liposomes is 10%/24 hr to 70%/24 hr in blood plasma at 37° C.,
   the drug is an anticancer agent which is gemcitabine,
   lipids constituting the liposomes include at least hydrogenated soybean phosphatidylcholine, 1,2-distearoyl-3-phosphatidylethanolamine-polyethylene glycol, and cholesterol, and
   the release rate of the drug from the liposomes is 10%/24 hr or less in physiological saline containing no blood components at 37° C.

2. The liposome composition according to claim 1, wherein the average particle size of the liposomes is 5 nm to 100 nm.

3. A pharmaceutical composition comprising the liposome composition according to claim 1.

4. A pharmaceutical composition comprising the liposome composition according to claim 2.

5. A method for producing a liposome composition according to claim 1, comprising:
   an emulsifying step of emulsifying lipids dissolved in an organic solvent to form liposomes, without a drying and solidifying step;
   a drug loading step of encapsulating the drug in the liposomes obtained in the emulsifying step; and
   an osmotic pressure adjusting step of replacing an unencapsulated drug aqueous solution with a hypo-osmotic solution to adjust the osmotic pressure of the inner water phase to be hyper-osmotic relative to the osmotic pressure of the outer water phase.

6. The method for producing a liposome composition according to claim 5, wherein the osmotic pressure adjusting step adjusts the osmotic pressure of the inner water phase of the liposomes to 3 fold to 5-fold relative to the osmotic pressure of the outer water phase.

7. The method for producing a liposome composition according to 5, wherein the liposomes obtained after the emulsifying step are used in a next step without extrusion processing.

8. The method for producing a liposome composition according to 6, wherein the liposomes obtained after the emulsifying step are used in a next step without extrusion processing.

9. The method for producing a liposome composition according to claim 5, wherein the drug loading step and the osmotic pressure adjusting step are carried out simultaneously.

* * * * *